(12) United States Patent
Ma et al.

(10) Patent No.: US 9,686,061 B2
(45) Date of Patent: *Jun. 20, 2017

(54) METHOD AND SYSTEM USING RELAYS WITH AGGREGATED SPECTRUM

(71) Applicant: Apple Inc., Cupertino, CA (US)

(72) Inventors: Jianglei Ma, Kanata (CA); Hang Zhang, Nepean (CA); Ming Jia, Ottawa (CA); Wen Tong, Ottawa (CA); Hua Xu, Ottawa (CA); Peiying Zhu, Kanata (CA)

(73) Assignee: Apple Inc., Cupertino, CA (US)

(*) Notice: Subject to any disclaimer, the term of this patent is extended or adjusted under 35 U.S.C. 154(b) by 658 days.

This patent is subject to a terminal disclaimer.

(21) Appl. No.: 13/944,365

(22) Filed: Jul. 17, 2013

(65) Prior Publication Data

US 2014/0050144 A1  Feb. 20, 2014

Related U.S. Application Data

(63) Continuation of application No. 12/996,189, filed as application No. PCT/CA2009/000836 on Jun. 12, 2009, now Pat. No. 8,804,598.

(Continued)

(51) Int. Cl.
*H04W 52/14* (2009.01)
*H04L 5/00* (2006.01)
(Continued)

(52) U.S. Cl.
CPC ............ *H04L 5/0039* (2013.01); *A61K 9/209* (2013.01); *A61K 9/2081* (2013.01);
(Continued)

(58) Field of Classification Search
None
See application file for complete search history.

(56) References Cited

U.S. PATENT DOCUMENTS 6,088,592 A    7/2000 Doner et al.
7,796,546 B2   9/2010 Lee et al.
(Continued)

FOREIGN PATENT DOCUMENTS

EP    1677443 A1   7/2006
EP    1777877 A2   4/2007
(Continued)

OTHER PUBLICATIONS

Office Action from Japanese Application No. 2014109294, issued Apr. 6, 2015, Japanese and English versions, pp. 1-7.
(Continued)

*Primary Examiner* — Candal Elphenord
(74) *Attorney, Agent, or Firm* — Meyertons, Hood, Kivlin, Kowert & Goetzel, P.C.

(57) ABSTRACT

International Mobile Telecommunications (IMT) Advanced technology, also known as 4th Generation (4G) targets to support up to 100 MHz BW. LTE currently supports single carrier bandwidths of up to 20 MHz. The present application describes a multi-carrier approach in which some embodiments of the invention provide a simple solution of aggregating multiple single carrier bandwidths to obtain a wider bandwidth (>20 MHz). Such an approach may extend Long Term Evolution (LTE) bandwidth to greater than that provided by a single carrier, yet maintain full backward compatibility with technologies that predate 4G technology and utilize smaller, single carrier bandwidths. More generally, embodiments of the invention can apply to other communication standards than only LTE.

20 Claims, 12 Drawing Sheets

Related U.S. Application Data

(60) Provisional application No. 61/060,995, filed on Jun. 12, 2008.

(51) Int. Cl.

| | | |
|---|---|---|
| *H04B 7/155* | (2006.01) | |
| *H04L 5/14* | (2006.01) | |
| *H04L 25/20* | (2006.01) | |
| *H04W 72/04* | (2009.01) | |
| *A61K 45/06* | (2006.01) | |
| *A61K 9/20* | (2006.01) | |
| *A61K 9/24* | (2006.01) | |
| *A61K 31/455* | (2006.01) | |
| *A61K 31/54* | (2006.01) | |
| *H04W 84/04* | (2009.01) | |
| *A61K 9/28* | (2006.01) | |
| *A61K 9/50* | (2006.01) | |

(52) U.S. Cl.
CPC ............ *A61K 31/455* (2013.01); *A61K 31/54* (2013.01); *A61K 45/06* (2013.01); *H04B 7/15542* (2013.01); *H04L 5/003* (2013.01); *H04L 5/0007* (2013.01); *H04L 5/14* (2013.01); *H04L 25/20* (2013.01); *H04W 52/143* (2013.01); *H04W 72/0453* (2013.01); *A61K 9/2886* (2013.01); *A61K 9/5026* (2013.01); *A61K 9/5073* (2013.01); *A61K 9/5084* (2013.01); *H04W 84/047* (2013.01)

(56) References Cited

U.S. PATENT DOCUMENTS

| | | | |
|---|---|---|---|
| 8,010,041 B2 | 8/2011 | Wang et al. | |
| 8,018,893 B2 | 9/2011 | Sartori et al. | |
| 8,036,099 B2 * | 10/2011 | Zangi ................... | H04L 5/0023 370/208 |
| 8,068,456 B2 | 11/2011 | Yomo et al. | |
| 8,139,526 B2 | 3/2012 | Zhou et al. | |
| 8,204,018 B2 | 6/2012 | Chindapol et al. | |
| 8,248,941 B2 | 8/2012 | Teyeb et al. | |
| 8,355,734 B2 | 1/2013 | Naden et al. | |
| 2004/0048574 A1 | 3/2004 | Walker et al. | |
| 2006/0135075 A1* | 6/2006 | Tee ....................... | H04L 5/0007 455/67.13 |
| 2006/0193280 A1 | 8/2006 | Lee et al. | |
| 2006/0203793 A1 | 9/2006 | Li et al. | |
| 2006/0209671 A1* | 9/2006 | Khan ................. | H04B 7/15542 370/208 |
| 2007/0081502 A1 | 4/2007 | Lee et al. | |
| 2007/0086368 A1 | 4/2007 | Lee et al. | |
| 2007/0155315 A1 | 7/2007 | Lee et al. | |
| 2007/0168482 A1 | 7/2007 | Chen et al. | |
| 2008/0063097 A1* | 3/2008 | Horiuchi ............ | H04B 7/15542 375/260 |
| 2008/0107062 A1 | 5/2008 | Viorel et al. | |
| 2008/0165719 A1* | 7/2008 | Visotsky .............. | H04B 7/2606 370/315 |
| 2008/0240275 A1 | 10/2008 | Cai | |
| 2009/0143088 A1* | 6/2009 | Einhaus .............. | H04L 27/2601 455/509 |
| 2010/0008287 A1* | 1/2010 | Lin ........................ | H04B 7/022 370/315 |
| 2010/0278136 A1 | 11/2010 | Oyman et al. | |
| 2010/0278221 A1* | 11/2010 | Qi ......................... | H04L 5/0007 375/219 |

FOREIGN PATENT DOCUMENTS

| | | |
|---|---|---|
| EP | 1890505 A1 | 2/2008 |
| EP | 1919143 A2 | 5/2008 |
| JP | 2007116703 A | 5/2007 |
| WO | 2005067173 A1 | 7/2005 |
| WO | 2009149565 A1 | 12/2009 |

OTHER PUBLICATIONS

Office Action from Korean Application No. 10-2011-7000714, issued Apr. 17, 2015, Korean and English versions, pp. 1-12.
Int'l Application PCT/CA2009/000836, Written Opinion of the International Searching Authority, mailed Oct. 19, 2009.
JP Application 2011-512798, Final Office Action (with English translation), issued Feb. 25, 2014.
CN Application 200980131692.0, First Office Action and Search Report (with English translation), issued Mar. 11, 2013.
CN Application 200980131692.0, Second Office Action (with English translation), issued Dec. 5, 2013.
JP Application 2011-512798, First Office Action (with English translation), issued Jul. 21, 2013.
EP Application 09761223.8, Extended European Search Report, mailed Feb. 13, 2012.
Nortel Networks, "Technologies for LTE-Advanced from RAN1 Perspectives," TSG-RAN1 #53, R1-081828, Agenda Item 6.2, May 5-9, 2008, pp. 1-18.
Panasonic, "Technical Proposals and Considerations for LTE Advanced," 3GPP TSG RAN WG1 Meeting #53, R1-081791, May 5-9, 2008, pp. 2-17.
Ericsson, "A Discussion on Some Technology Components for LTE-Advanced," TSG-RAN WG1 #53, R1-082024, Agenda Item 6.2, May 5-9, 2008, pp. 2-12.
Int'l Application PCT/CA2009/000836, International Search Report, mailed Oct. 19, 2009.
Office Action, Korean Application No. 10-2014-7007819, mailed Nov. 27, 2015, 11 pages.

* cited by examiner

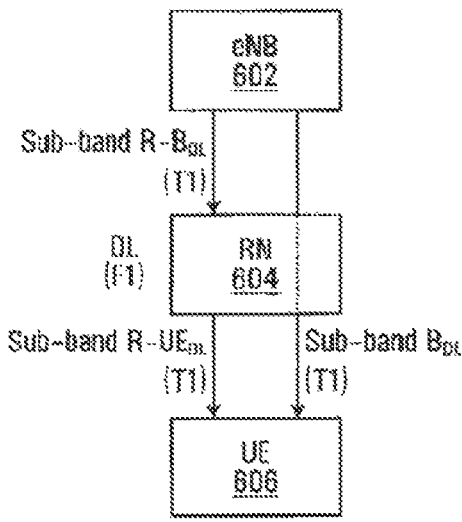
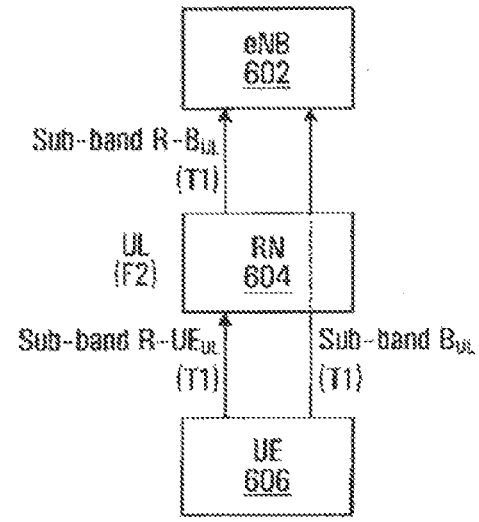
Figure 6A                Figure 6B
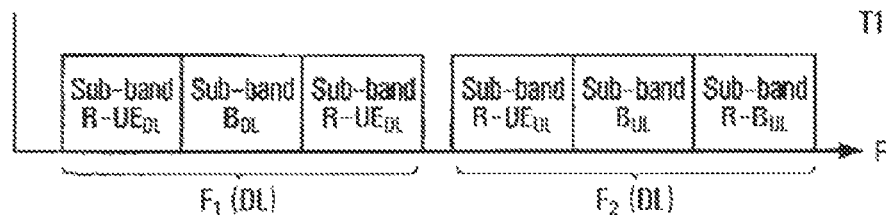
Figure 6C

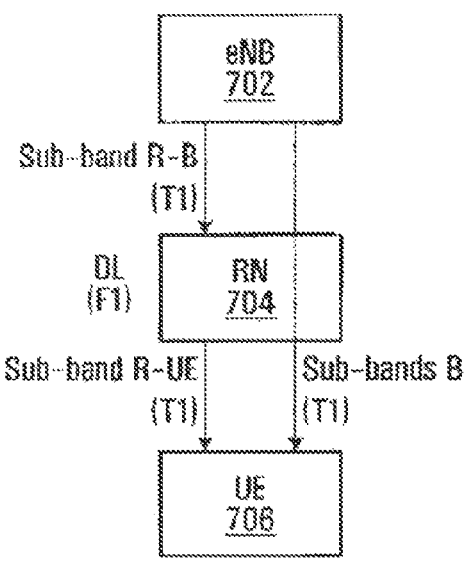
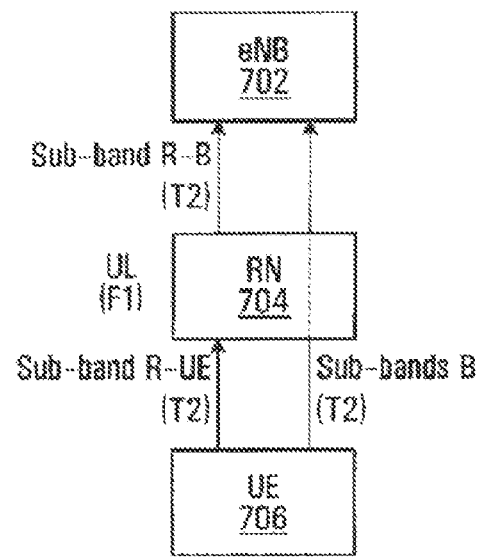
Figure 7A      Figure 7B
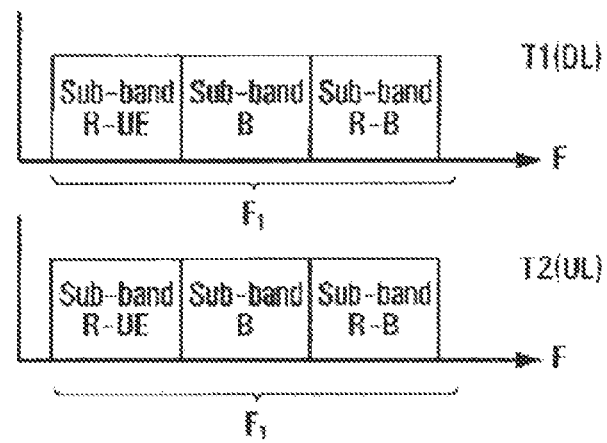
Figure 7C

METHOD AND SYSTEM USING RELAYS WITH AGGREGATED SPECTRUM

PRIORITY CLAIM

This application is a continuation of and claims the benefit of priority from U.S. patent application Ser. No. 12/996,189, entitled "Method and System using Relays with Aggregated Spectrum" and filed on Dec. 3, 2010, which is a National Stage of and claims the benefit of priority from International Application No. PCT/CA2009/000836, entitled "Method and System using Relays with Aggregated Spectrum" and filed on Jun. 12, 2009, which claims the benefit of priority from U.S. Provisional Patent Application Ser. No. 61/060, 995, filed on Jun. 12, 2008, all of which are fully incorporated herein by reference for all purposes.

BACKGROUND

Field of the Application

The invention relates to relays in wireless communication networks.

Background of the Disclosure

A relay station acts as an intermediary between a base station and a mobile station by communicating with the base station and mobile station. In addition, the relay station may act as an intermediary between a base station and a second relay station by communicating with the base station and the second relay station or between a second relay station and a mobile station by communicating with the second relay station and the mobile station. To avoid self-interference between a transmitter and receiver in the relay station, usually the relay station cannot receive data and transmit data simultaneously in the same system operation band. Different time slots are allocated to the links from base station to relay station, from mobile station to relay station, or from relay station to relay station for both frequency division duplexing (FDD) and time division duplexing (TDD).

Some shortcomings of such a half-duplex FDD or TDD base relay transmission are:
1. a reduced efficiency of the system;
2. modification of frame structure in necessary to accommodate the half duplex nature of the transmissions;
3. difficulty in supporting synchronous HARQ; and
4. difficulty in monitoring all mobile stations.

SUMMARY

In accordance with a first aspect of the invention there is provided a method comprising: for a communication link between a base station and at least one relay station with which the base station is communicating, allocating a first frequency sub-band; for a communication link between the base station and a first subset of one or more mobile stations with which the base station is communicating, allocating a second frequency sub-band; for a communication link between the at least one relay station and a second subset of one or more mobile stations with which the at least one relay station is communicating, allocating a third frequency sub-band; the at least one relay station performing at least one of: receiving signals on the first frequency sub-band and transmitting signals on the third frequency sub-band simultaneously; and transmitting signals on the first frequency sub-band and receiving signals on the third frequency sub-band simultaneously; wherein the first, second and third frequency sub-bands are aggregate non-overlapping sub-bands that collectively provide increased bandwidth.

In some embodiments, one or more of the first, second and third frequency sub-band include first, second and third carrier frequencies, respectively.

In some embodiments, one or more of the first, second and third carrier frequencies are non-contiguous carrier frequencies within the aggregate increased bandwidth.

In some embodiments, the first, second and third frequency sub-bands are contiguous sub-bands within the aggregate increased bandwidth.

In some embodiments, allocating the first frequency sub-band comprises allocating in a down link (DL) frequency band a first DL frequency sub-band and in an uplink (UL) frequency band a first UL frequency sub-band; allocating the second frequency sub-band comprises allocating in the DL frequency band a second DL frequency sub-band and in the UL frequency band a second UL frequency sub-band; allocating the third frequency sub-band comprises allocating in the DL frequency band a third DL frequency sub-band and in the UL frequency band a third UL frequency sub-band; the at least one relay station performing one or more of: receiving signals on the first DL frequency sub-band, transmitting signals on the third DL frequency sub-band, transmitting signals on the first UL frequency sub-band and receiving signals on the third UL frequency sub-band simultaneously in a same time slot.

In some embodiments, in a first time slot for down link (DL) communications, allocating in a frequency band the first frequency sub-band, the second frequency sub-band and the third frequency sub-band; in a second time slot for uplink (UL) communications, allocating in the frequency band the first frequency sub-band, the second frequency sub-band and the third frequency sub-band; the at least one relay station performing: receiving signals on the first frequency sub-band and transmitting signals on the third frequency sub-band simultaneously during a first time slot; and transmitting signals on the first frequency sub-band and receiving signals on the third frequency sub-band simultaneously in a same time slot.

In some embodiments the method further comprises at least one of: allocating the first frequency sub-band comprises allocating a dedicated sub-band; and allocating the third frequency sub-band comprises allocating a dedicated sub-band.

In some embodiments the method further comprises: dynamically assigning at least one of the first and third sub-band to a different sub-band than the dedicated first or third frequency sub-band, respectively.

In some embodiments the method further comprises: changing the size of the sub-band of at least one of the first, second and third frequency sub-bands.

In some embodiments, the method further comprises: changing the number of carriers included in at least one of the first, second and third carriers.

In some embodiments, the first, second and third frequency sub-bands are each greater than 10 MHz and less than 30 MHz.

In some embodiments, the relay station is an LTE enabled relay station.

In some embodiments, the LTE enabled relay station configured to support legacy mobile stations.

In some embodiments, the method further comprises: applying transmission power distribution control to reduce the interference between transmissions and receptions of the relay station.

In some embodiments, applying transmission power distribution control comprises: transmitting signals on the first or third frequency sub-bands using a narrow band signal with a higher power than a wide band signal having a lower power, to reduce to the size of a guard band between transmissions and receptions of the relay station.

In accordance with a second aspect of the invention, there is provided a relay station comprising; at least one antenna; transmit circuitry coupled to the at least one antenna configured to transmit a signal; receive circuitry coupled to the at least one antenna configured to receive a signal; relay circuitry configured to: for a communication link between a base station with which the relay station is communicating and the relay station, allocate a first frequency sub-band; for a communication link between the relay station and a set of one or more mobile stations with which the relay station is communicating, allocate a second frequency sub-band; the relay station configured to perform at least one of: receive signals on the first frequency sub-band and transmit signals on the second frequency sub-band simultaneously; and transmit signals on the first frequency sub-band and receive signals on the second frequency sub-band simultaneously; wherein the first and second frequency sub-bands are aggregate non-overlapping sub-bands that collectively provide increased bandwidth in conjunction with a third frequency sub-band for a communication link between the base station and a second set of one or more mobile stations with which the base station is communicating.

In some embodiments, one or more of the first, second and third frequency sub-band include first, second and third carrier frequencies, respectively.

In some embodiments, one or more of the first, second and third carrier frequencies are non-contiguous carrier frequencies within the aggregate increased bandwidth.

In some embodiments, the first, second and third frequency sub-bands are contiguous sub-bands within the aggregate increased bandwidth.

In some embodiments, the relay station is further configured to allocate in a down link (DL) frequency band a first DL frequency sub-band and in an uplink (UL) frequency band a first UL frequency sub-band; allocate in the DL frequency band a second DL frequency sub-band and in the UL frequency band a second UL frequency sub-band; the relay station configured to perform one or more of: receive signals on the first DL frequency sub-band, transmit signals on the second DL frequency sub-band, transmit signals on the first UL frequency sub-band and receive signals on the second UL frequency sub-band simultaneously in a same time slot.

In some embodiments, the relay station is further configured to: in a first time slot for down link (DL) communications, allocate in a frequency band the first frequency sub-band and the second frequency sub-band; in a second time slot for uplink (UL) communications, allocate in the frequency band the first frequency sub-band and the second frequency sub-band; the relay station configured to perform: receive signals on the first frequency sub-band and transmit signals on the second frequency sub-band simultaneously during the first time slot; and transmit signals on the first frequency sub-band and receive signals on the second frequency sub-band simultaneously in the second time slot.

In some embodiments, the relay station is further configured to: allocate the first frequency sub-band as a dedicated sub-band; and allocate the second frequency sub-band as a dedicated sub-band.

In some embodiments, the relay station is further configured to: dynamically assign at least one of the first and second frequency sub-bands to a different sub-band than the dedicated first or second frequency sub-band, respectively.

In some embodiments, the relay station is further configured to: change the size of the sub-band of at least one of the first or second frequency sub-bands.

In some embodiments, the relay station is further configured to: change the number of carriers included in at least one of the first and second carriers.

In accordance with a third aspect of the invention, there is provided a base station comprising: at least one antenna; transmit circuitry coupled to the at least one antenna configured to transmit a signal; receive circuitry coupled to the at least one antenna configured to receive a signal; base station circuitry configured to: for a communication link between the base station and at least one relay station with which the at least one relay station is communicating, allocate a first frequency sub-band; for a communication link between the base station and a first subset of one or more mobile stations with which the base station is communicating, allocate a second frequency sub-band; for a communication link between the at least one relay station and a second subset of one or more mobile stations with which the at least one relay station is communicating, allocate a third frequency sub-band; the base station configure to notify the relay station regarding the location of the allocated first, second and third sub-bands; wherein the first, second and third frequency sub-bands are aggregate non-overlapping sub-bands that collectively provide increased bandwidth.

In some embodiments, one or more of the first, second and third frequency sub-band include first, second and third carrier frequencies, respectively.

In some embodiments, one or more of the first, second and third carrier frequencies are non-contiguous carrier frequencies within the aggregate increased bandwidth.

In some embodiments, the first, second and third frequency sub-bands are contiguous sub-bands within the aggregate increased bandwidth.

In some embodiments, the base station is further configured to: allocate in a down link (DL) frequency band a first DL frequency sub-band and in an uplink (UL) frequency band a first UL frequency sub-band; allocate in the DL frequency band a second DL frequency sub-band and in the UL frequency band a second UL frequency sub-band; allocate in the DL frequency band a third DL frequency sub-band and in the UL frequency band a third UL frequency sub-band.

In some embodiments, the base station is further configured to: in a first time slot for down link (DL) communications, allocate in a frequency band the first frequency sub-band, the second frequency sub-band and the third frequency sub-band; in a second time slot for uplink (UL) communications, allocate in the frequency band the first frequency sub-band, the second frequency sub-band and the third frequency sub-band.

In some embodiments, the base station is further configured to: allocate the first frequency sub-band as a dedicated sub-band; and allocate the third frequency sub-band as a dedicated sub-band.

In some embodiments, the base station is further configured to: dynamically assign at least one of the first and third sub-bands to a different sub-band than the dedicated first or third sub-band, respectively.

In some embodiments, the base station is further configured to: change the size of the sub-band of at least one of the first, second and third sub-bands.

In some embodiments, the base station is further configured to: change the number of carriers included in at least one of the first, second and third carriers.

In accordance with a fourth aspect of the invention, there is provided a communication system comprising: at least one base station; at least one relay station in communication with the at least one base station; a first set of one or more mobile stations in communication with the at least one base station; a second set of one or more mobile stations in communication with the at least one relay station; for a communication link between a base station of the at least one base station and the at least one relay station with which the base station is communicating, allocating a first frequency sub-band; for a communication link between the base station and the first set of one or more mobile stations with which the base station is communicating, allocating a second frequency sub-band; for a communication link between the at least one relay station and the second set of one or more mobile stations with which the at least one relay station is communicating, allocating a third frequency sub-band; the at least one relay station performing at least one of: receiving signals on the first frequency sub-band and transmitting signals on the third frequency sub-band simultaneously; and transmitting signals on the first frequency sub-band and receiving signals on the third frequency sub-band simultaneously; wherein the first, second and third frequency sub-bands are aggregate non-overlapping sub-bands that collectively provide increased bandwidth.

In some embodiments, one or more of the first, second and third frequency sub-band include first, second and third carrier frequencies, respectively.

In some embodiments, one or more of the first, second and third carrier frequencies are non-contiguous carrier frequencies within the aggregate increased bandwidth.

In some embodiments, the first, second and third frequency sub-bands are contiguous sub-bands within the aggregate increased bandwidth.

In some embodiments, allocating the first frequency sub-band comprises allocating in a down link (DL) frequency band a first DL frequency sub-band and in an uplink (UL) frequency band a first UL frequency sub-band; allocating the second frequency sub-band comprises allocating in the DL frequency band a second DL frequency sub-band and in the UL frequency band a second UL frequency sub-band; allocating the third frequency sub-band comprises allocating in the DL frequency band a third DL frequency sub-band and in the UL frequency band a third UL frequency sub-band; the at least one relay station performing one or more of receiving signals on the first DL frequency sub-band, transmitting signals on the third DL frequency sub-band, transmitting signals on the first UL frequency sub-band and receiving signals on the third UL frequency sub-band simultaneously in a same time slot.

In some embodiments, in a first time slot for down link (DL) communications, allocating in a frequency band the first frequency sub-band, the second frequency sub-band and the third frequency sub-band; in a second time slot for uplink (UL) communications, allocating in the frequency band the first frequency sub-band, the second frequency sub-band and the third frequency sub-band; the at least one relay station performing: receiving signals on the first frequency sub-band and transmitting signals on the third frequency sub-band simultaneously during the first time slot, transmitting signals on the first frequency sub-band and receiving signals on the third frequency sub-band simultaneously in the second time slot.

In some embodiments, the system further comprises at least one of: allocating the first frequency sub-band comprises allocating a dedicated sub-band; and allocating the third frequency sub-band comprises allocating a dedicated sub-band.

In some embodiments, the system further comprises dynamically assigning at least one of the first and third sub-bands to a different sub-band than the dedicated first or third frequency sub-band, respectively.

In some embodiments, the system further comprises changing the size of the sub-band of at least one of the first, second and third frequency sub-bands.

In some embodiments, the system further comprises changing the number of carriers included in at least one of the first, second and third carriers.

In some embodiments, the first, second and third frequency sub-bands are each greater than 10 MHz and less than 30 MHz.

In some embodiments, the relay station is an LTE enabled relay station.

In some embodiments, the LTE enabled relay station is configured to support legacy mobile stations.

In some embodiments, the system further comprises applying transmission power distribution control to reduce the interference between transmissions and receptions of the relay station.

In some embodiments, applying transmission power distribution control comprises: transmitting signals on the first or third sub-bands using a narrow band signal with a higher power than a wide band signal having a lower power, to reduce to the size of a guard band between transmissions and receptions of the relay station.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the invention will now be described with reference to the attached drawings in which:

FIGS. 6a, 6b and 6c are block diagrams of examples of DL FDD in-band communications and UL FDD in-band communications between a base station and a mobile station via a relay station according to an embodiment of the invention;

FIGS. 7a, 7b and 7c are block diagrams of examples of DL TDD in-band communications and UL FDD in-band communications between a base station and a mobile station via a relay station according to an embodiment of the invention;

DETAILED DESCRIPTION OF THE EMBODIMENTS OF THE INVENTION

Figure 1:
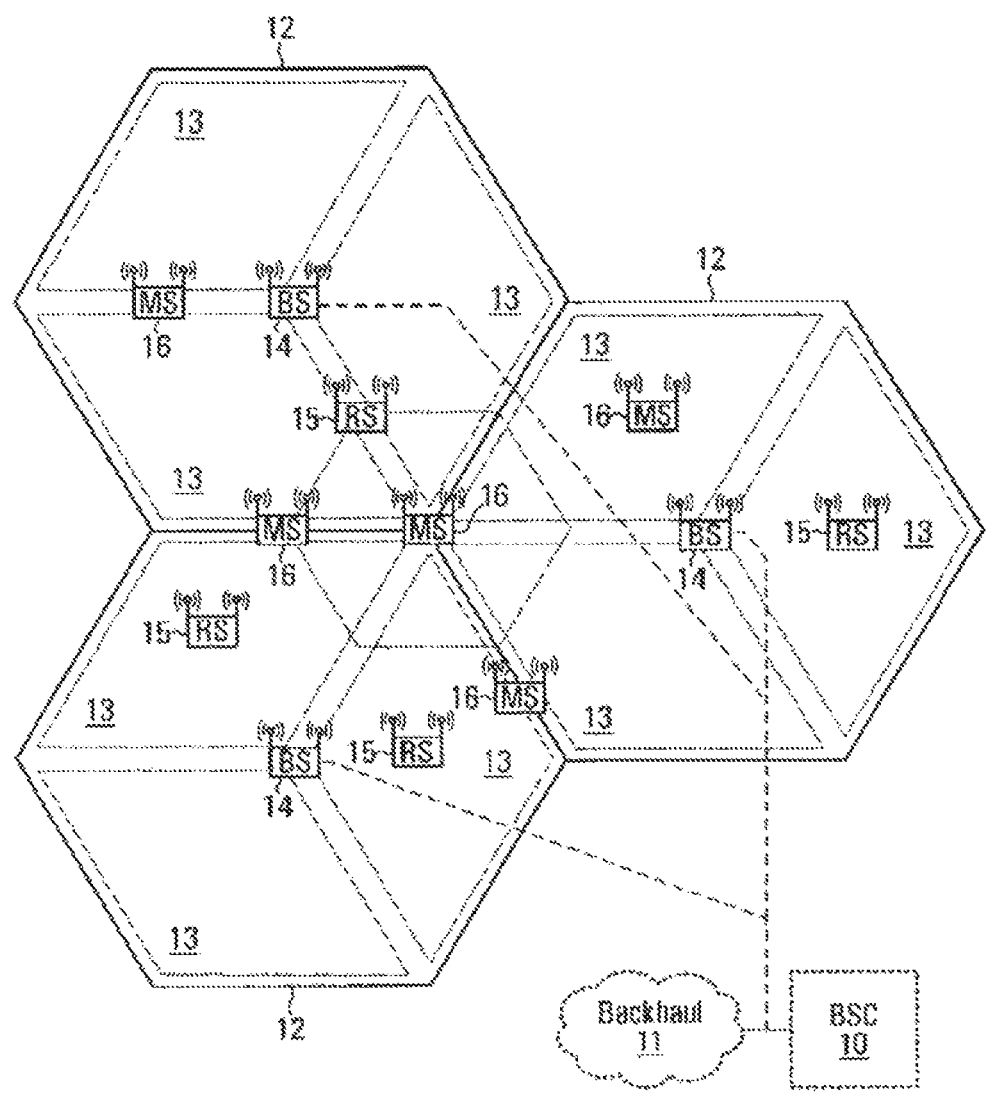
FIG. 1 is a block diagram of a cellular communication system.

Referring to the drawings, FIG. 1 shows a base station controller (BSC) 10 which controls wireless communications within multiple cells 12, which cells are served by corresponding base stations (BS) 14. In some configurations, each cell is further divided into multiple sectors 13 or zones (not shown). In general, each base station 14 facilitates communications using OFDM with mobile and/or wireless terminals 16, which are within the cell 12 associated with the corresponding base station 14. The movement of the mobile terminals 16 in relation to the base stations 14 results in significant fluctuation in channel conditions. As illustrated, the base stations 14 and mobile terminals 16 may include multiple antennas to provide spatial diversity for communications. In some configurations, relay stations 15 may assist in communications between base stations 14 and wireless terminals 16. Wireless terminals 16 can be handed off 18 from any cell 12, sector 13, zone (not shown), base station 14 or relay 15 to another cell 12, sector 13, zone (not shown), base station 14 or relay 15. In some configurations, base stations 14 communicate with each and with another network (such as a core network or the internet, both not shown) over a backhaul network 11. In some configurations, a base station controller 10 is not needed.

International Mobile Telecommunications (IMT) Advanced technology, also known as $4_{th}$ Generation (4G) targets to support up to 100 MHz BW. LTE currently supports single carrier bandwidths of up to 20 MHz. The present application describes a multi-carrier approach in which some embodiments of the invention provide a simple solution of aggregating multiple single carrier bandwidths to obtain a wider bandwidth (>20 MHz). Such an approach may extend Long Term Evolution (LTE) bandwidth to greater than that provided by a single carrier, yet maintain full backward compatibility with technologies that predate 4G technology and utilize smaller, single carrier bandwidths.

A relay station that can both transmit and receive simultaneously may be included in the spectrum aggregated communication system to optimize system performance possibly by using one or more of the following approaches:

1. maintaining non-interrupted bi-directional communications links between a base station and at least one relay station as well as between a relay station and at least one mobile station;
2. using a dedicated carrier based relay station for non-contiguous spectrum aggregation for time divisional duplexing (TDD) and/or frequency division duplexing (FDD);
3. using a dedicated sub-band based relay station for contiguous spectrum aggregation for TDD and/or FDD;
4. using flexible channel resource allocations for at least one relay station and at least one mobile station;
5. using carrier hopping and/or sub-band hopping for supporting legacy mobile stations;
6. using transmission power distribution control to reduce interference between simultaneous transmitting and receiving in at least one relay station; and
7. controlling the separation of the available guard band between carriers and/or sub-bands used for simultaneous transmitting and receiving.

A relay station may be used to improve cell coverage and throughput for LTE. As communication between the relay station and mobile stations occur in the aggregated bandwidth that also includes bandwidth for communications between the base station and mobile stations, the relay station communications are considered in-band communications.

Some embodiments of the invention provide schemes to more efficiently introduce the use of relay stations into broad band LTE-A communication systems.

While embodiments of the invention have been described above with regard to LTE-A, it is to be understood that embodiments of the invention may be applicable to other types of communication standards.

Spectrum aggregation can be realized by aggregating contiguous and/or non-contiguous spectrum in different bands. Some embodiments of the invention may be implemented by aggregating non-contiguous single carrier bands. In such embodiments, separate and non-overlapping carriers are allocated for communication between the base station and mobile stations that the base station communicates with directly which are a single hop from the base station, for communication between the base station and at least one relay station that the base station communicates with directly which is a single hop from the base station, and for communication between the at least one relay station and mobile stations that the at least one relay station communicates with directly which are at least two hops away from the base station. One or more carriers may be used for base station to mobile station communications, base station to relay station communications, relay station to relay station communications, and relay station to mobile station communications. In addition, carriers may be allocated for communication between a relay one hop away from the base station and a relay two hops away from the base station and for communication between with the relay two hops away from the base station and one or more mobile stations that the two hop away relay may communicate with. In some embodiments, not all of the carriers within the aggregate spectrum band are used for communication. Any unutilized carriers result in gaps between the carriers that are used. Such an arrangement is therefore considered "non-contiguous", as not all of the carriers are utilized.

Some embodiments of the invention may be implemented by aggregating contiguous sub-bands. The sub-bands are allocated for communication between the base station and mobile stations that the base station communicates with directly which are a single hop from the base station, for communication between the base station and at least one relay station that the base station communicates with directly which is a single hop from the base station, and for communication between the at least one relay station and mobile stations that the at least one relay station communicates with directly which are at least two hops away from the base station. In addition, sub-bands may be allocated for communication between a relay one hop away from the base station and a relay two hops away from the base station and for communication between with the relay two hops away from the base station and one or more mobile stations that the two hop away relay may communicate with. When all of the sub-bands in the aggregated spectrum are used in the manner described above, the result is that the sub-bands are arranged in a "contiguous" manner.

Relay Station for Non-Contiguous Spectrum Aggregation

In some embodiments, in a non-contiguous spectrum aggregation scenario, a relay station is supported by reserving a dedicated carrier (Carrier R-B) for communications between the relay station and the base station. In some embodiments, in a non-contiguous spectrum aggregation scenario, a relay station is supported by dynamically scheduling a carrier (Carrier R-B) for data exchange between the base station and the relay station.

To reduce in-band transmit/receive interference at the relay station, carriers (Carrier R-B) used for communication between the base station and one hop away relay stations should be spaced apart from neighbor carriers. In some embodiments, guard bands are in place between the carriers. Neighbor carriers may include carriers (Carrier B) used for communication between the base station and one hop away mobile stations (Carrier B). Neighbour carriers may also include carriers (Carrier R-UE) used for communication between the relay station and one or more mobile stations with which the relay station may be communicating. The farther apart that Carrier R-B and Carrier R-UE are spaced, the greater amount of reduction of in-band transmit/receive interference should occur. In some embodiments, there are alternative ways to reduce interference rather than a large guard band, such as transmission power distribution control, which will be discussed below.

Figure 2:
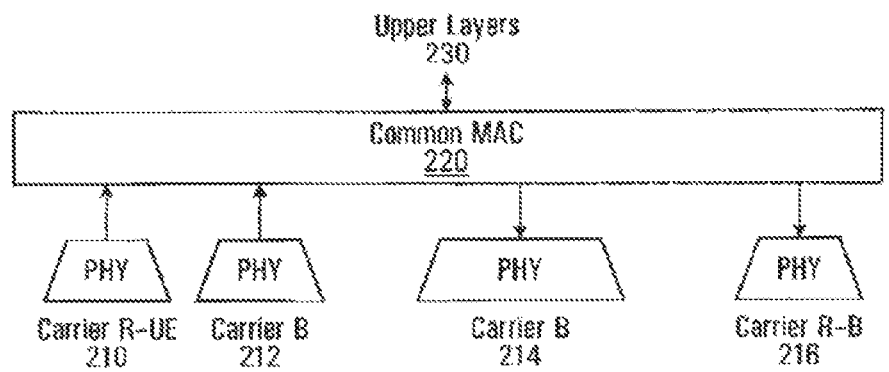
FIG. 2 is a schematic diagram representing different layers utilized in network communications for an example of a non-contiguous spectrum aggregation according to an embodiment of the invention.

FIG. 2 illustrates a schematic diagram representing different layers utilized in network communications. In the physical layer (PHY), which includes the basic hardware transmission technologies used in the network, the respective carriers, Carrier R-UE 210, Carrier B 212,214 and Carrier R-B 216, are illustrated as separate, non-overlapping carriers. The media access layer (MAC) 220, which is a sub-layer of the data link layer and provides addressing and channel access control mechanisms that make it possible for network nodes to communicate within the network, is illustrated as common to all the PHY layer carriers in the aggregated spectrum. That is the MAC layer is adapted to have access to all the separate carriers and by collectively utilizing the carriers, provide an increased bandwidth. The common MAC layer is illustrated as being in communication with upper layers 230 in the network hierarchy.

In some embodiments, the base station communicating with the one or more relay station allocates the carrier locations in the aggregated spectrum to be used for Carrier R-B, Carrier R-UE and Carrier B. In some embodiments a relay station may provide the base station with information to aid in identifying carrier locations and/or a number of carriers that are needed with respect to at least one of Carrier R-B and Carrier R-UE.

In some embodiments, more than one carrier can be assigned as Carrier R-B. The number of Carrier R-B's may be adjusted according to the bandwidth requirement for communications between the base station and the at least one relay station.

In some embodiments, more than one carrier can be assigned as Carrier R-UE. The number of Carrier R-UE's may be adjusted according to the bandwidth requirement for communications between a relay station and at least one mobile station with which the relay station is communicating.

In some embodiments, more than one carrier can be assigned as Carrier B. The number of Carrier B's may be adjusted according to the bandwidth requirement for communications between the base station and at least one mobile station one hop away from the base station with which the base station is communicating.

In some embodiments, for supporting legacy mobile stations, in particular, but not limited to the case in which legacy mobile stations are allocated specific carriers in the aggregate spectrum that may not align with a desired carrier location in an LTE-A enabled network, the locations of Carrier R-B and Carrier R-UE may change from time to time to accommodate the legacy mobile stations and/or the relay stations that are in communication with the legacy mobile stations.

In some embodiments, the change of carrier locations to support legacy users (carrier hopping) of relay links occurs on a time slot by time slot basis. In some embodiments, one or more consecutive time slots have a first carrier location arrangement in the aggregate spectrum and a subsequent one or more consecutive time slots have a second carrier location arrangement in the aggregate spectrum to support the legacy mobile stations, which is different than the first carrier location arrangement. This arrangement of time slots having different carrier location arrangements may be repeated over time. In some embodiments, the second carrier location arrangement of subsequent repetitions of the second carrier location arrangement may change over time. In some embodiments, the number of time slots of either the first or second carrier location arrangements can vary in number. In some embodiments, more than two groups of one or more time slots may be used, each group of one or more time slots having a different carrier location arrangement.

In some embodiments, one or more carrier locations of the aggregate spectrum use time division duplexing to separate relay station reception and transmission in the time domain to support legacy mobile stations, while other carrier locations maintain a non-interrupted transmission and reception of communications between the relay station and the base station and/or between the relay station and one or more mobile station. In a particular example, referring to FIG. 2, in a first time slot a relay station receives communication on Carrier R-B 216 from a base station, but does not transmit on carrier R-B 216 to the base station, and in second time slot the relay station transmits communication on Carrier R-B 216 to the base station, but does not receive on carrier R-B 216 from the base station.

FDD In-Band Relay

One manner of maintaining non-interrupted bi-directional links between a base station and a relay station as well as bi-directional links between the relay station and one or more mobile station is a FDD in-band implementation.

Figures 3A, 3B:
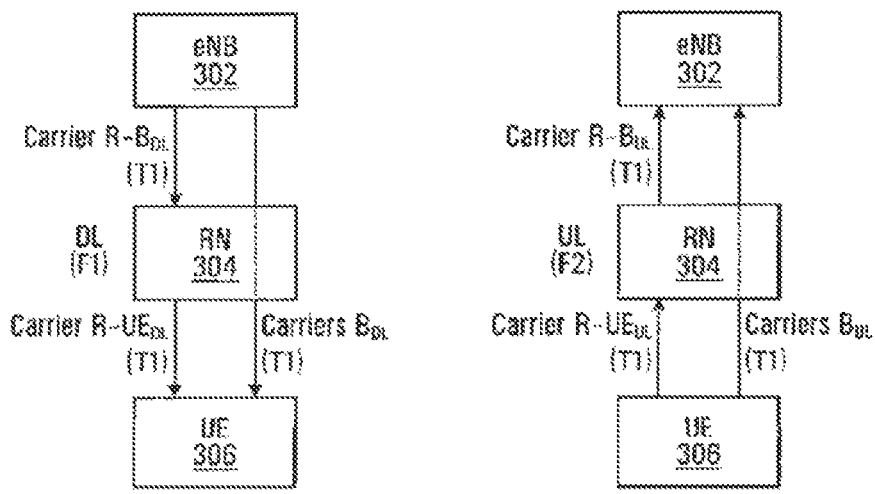
FIGS. 3a, 3b and 3c are block diagrams of examples of DL FDD in-band communications and UL FDD in-band communications between a base station and a mobile station via a relay station according to an embodiment of the invention.

Referring to FIGS. 3a and 3b, an FDD in-band implementation for non-contiguous aggregation spectrum will now be described.

FIG. 3a illustrates a block diagram representation of a base station (eNB) 302 communicating via a relay station (RN) 304 with a mobile station (UE) 306 in a down link (DL) direction from the base station 302 to the mobile station 306 using an aggregate spectrum. For a particular time slot T1, on a DL frequency band F1, the relay station 304 can simultaneously receive data from the base station 302 on Carrier R-B$_{DL}$, and transmit data to the mobile station 306 on Carrier R-UE$_{DL}$. Data transmitted from the base station 302 to mobile stations one hop away (not shown) from the base station 302 are transmitted on Carrier B$_{DL}$ within the in-band spectrum. As these signals do not dissipate at a distance equal to the relay station 304, they are illustrated continuing onto the mobile station 306. This does not necessarily mean that Carrier B$_{DL}$ will reach the mobile station that the relay station is communicating with. Carrier B$_{DL}$ is illustrated to indicate potential interference with Carrier R-B$_{DL}$ and Carrier R-UE$_{DL}$.

In some embodiments, the locations of the different carriers are maintained in the same positions for each time slot. In some embodiments, the locations of the different carriers are in different positions in different time slots, as described above. Such embodiments may be useful in supporting legacy mobile stations.

FIG. 3b illustrates a block diagram representation of the base station 302 communicating via the relay station 304 with the mobile station 306 in an uplink (UL) direction from the mobile station 306 to the base station 302. For the time slot T1, on a UL frequency band F2, the relay station 304 can simultaneously receive data from the mobile station 306 on Carrier R-UE$_{UL}$ and transmit data to the base station 302 on Carrier R-B$_{UL}$. Data transmitted from the mobile stations one hop away (not shown) from the base station 302 to the base station 302 are transmitted on Carrier B$_{UL}$ within the in-band spectrum. These signals may typically originate close to the base station or close to the relay station, but they are illustrated between the mobile station 306 and the base station 302. Carrier B$_{UL}$ is illustrated to indicate potential interference with Carrier R-B$_{UL}$ and Carrier R-UE$_{UL}$.

In some embodiments, the locations of the different carriers are maintained in the same positions for each time slot. In some embodiments, the locations of the different carriers are in different positions in different time slots, as described above.

Figure 3C:
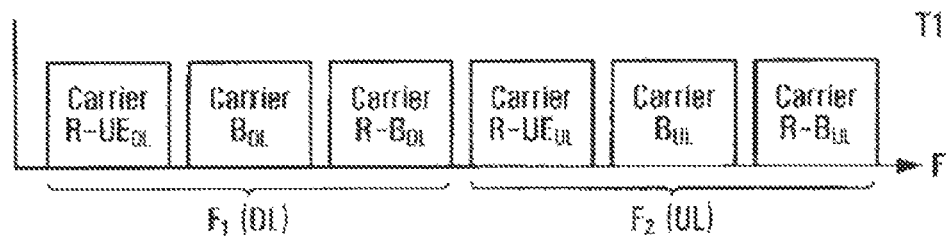

FIG. 3c illustrates an example spectrum pertaining to FIGS. 3a and 3b. FIG. 3c illustrates a DL frequency band F1, including Carrier R-UE$_{DL}$, Carrier B$_{DL}$, and carrier R-B$_{DL}$, and an UL frequency band F2, including Carrier R-UE$_{UL}$, Carrier B$_{UL}$ and Carrier R-B$_{UL}$.

In some embodiments, any of Carrier R-B$_{DL}$, Carrier R-UE$_{DL}$, Carrier R-B$_{UL}$, and Carrier R-UE$_{UL}$ can be re-used by the base station and relay station to further improve the spectrum efficiency. For example, in a base station transmitting over multiple sectors, Carrier R-B$_{DL}$ (or R-B$_{UL}$) may be reused in sectors that are well separated such that little to no interference would occur. Similarly, for a given base station, in sectors that are not in close proximity, Carrier R-UE$_{DL}$ (or R-UE$_{UL}$) may be re-used between relay stations and mobile stations.

TDD In-Band Relay

Another manner of maintaining non-interrupted bi-directional links between a base station and a relay station as well as bi-directional links between the relay station and one or more mobile station during DL and UL sub-frames is a TDD in-band implementation.

Figure 4A:
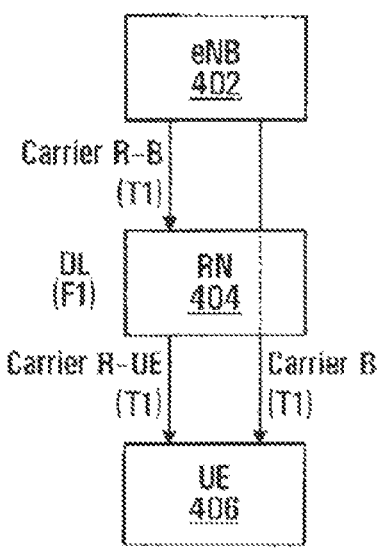
FIGS. 4a, 4b and 4c are block diagrams of examples of DL TDD in-band communications and UL FDD in-band communications between a base station and a mobile station via a relay station according to an embodiment of the invention.
Figure 4B:
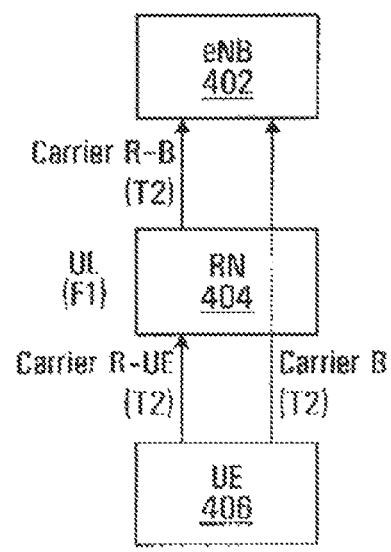

Referring to FIGS. 4a and 4b, a TDD in-band implementation for non-contiguous aggregation spectrum will now be described.

FIG. 4a illustrates a block diagram representation of a base station (eNB) 402 communicating via a relay station (RN) 404 with a mobile station (UE) 406 in a down link direction from the base station 402 to the mobile station 406. For a DL time slot T1, on a frequency band F1, the relay station 404 can simultaneously receive data from the base station 402 on Carrier R-B and transmit data to the mobile station 406 on Carrier R-UE. Data transmitted from the base station 402 to mobile stations one hop away (not shown) from the base station 402 are transmitted on Carrier B within the in-band spectrum. As these signals do not dissipate at a distance equal to the relay station 404, they are illustrated continuing onto the mobile station 406. This does not necessarily mean that Carrier B will reach the mobile station that the relay station is communicating with. Carrier B is illustrated to indicate potential interference with Carrier R-B and Carrier R-UE.

In some embodiments, the locations of different carriers are maintained in the same positions for each time slot. In some embodiments, the locations of different carriers are in different positions, as described above.

FIG. 4b illustrates a block diagram representation of the base station 402 communicating via the relay station 404 with the mobile station 406 in an uplink direction from the mobile station 406 to the base station 402. For a UL time slot T2, on the frequency band F1, the relay station 404 can simultaneously receive data from the mobile station 406 on Carrier R-UE and transmit data to the base station 402 on Carrier R-B. Data transmitted from the mobile stations one hop away (not shown) from the base station 402 to the base station 402 are transmitted on Carrier B within the in-band spectrum. These signals may typically originate close to the base station or close to the relay station, but they are illustrated between the mobile station 406 and the base station 402. Carrier B is illustrated to indicate potential interference with Carrier R-B and Carrier R-UE.

In some embodiments, the locations of different carriers being are maintained in the same positions for each time slot. In some embodiments, the locations of different carriers are in different positions, as described above.

While a single base station, single relay station and single mobile station are illustrated in FIGS. 3a, 3b, 4a and 4b, it is to be understood that a network may have multiple base stations, each base station communicating with one or more relay stations and possibly one or more one hop away mobile stations, each relay station communicating with one or more mobile station and possibly one or more second relay stations that may communicate with mobile stations.

In some embodiments, Carrier R-B and Carrier R-UE can be re-used by the base station and relay station to further improve the spectrum efficiency.

Figure 4C:
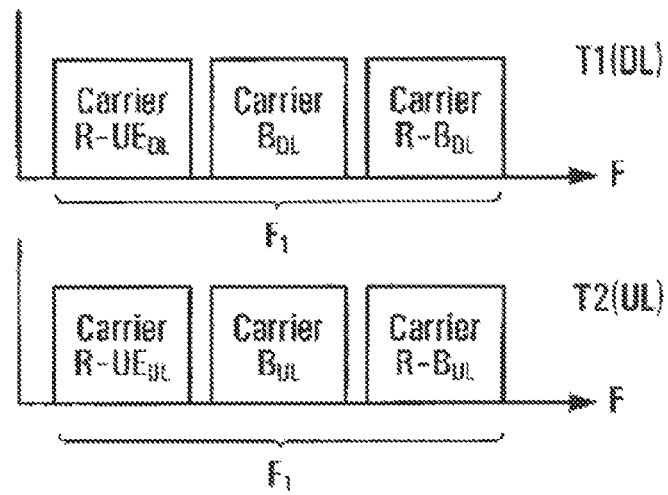

FIG. 4c illustrates an example aggregate spectrum for each of two time slots as described above with regard to FIGS. 4a and 4b. FIG. 4c illustrates a first time slot T1 in which DL communications occur on frequency band F1, which includes Carrier R-B, Carrier R-UE and Carrier B and a second time slot T2 in which UL communications occur on frequency band F1, which includes Carrier R-E, Carrier R-UE and Carrier B.

Relay for Contiguous Spectrum Aggregation

In some embodiments, in a contiguous spectrum aggregation scenario, a relay station can be supported by reserving a dedicated sub-band (Sub-band R-B) for communications between the relay station and the base station. In some embodiments, in a contiguous spectrum aggregation scenario, a relay station can be supported by dynamically scheduling a sub-baud (Sub-band R-B) for data exchange between the base station and the relay station.

To reduce in-band transmit/receive interference at the relay station, a sub-band (Sub-band R-B) used for communication between the base station and one hop away relay stations should be spaced apart from a sub-band (Sub-band R-UE) used for communication between the relay station and one or more mobile stations with which the relay station may be communicating. The farther apart that Sub-band R-B and Sub-band R-UE are spaced, the greater amount of reduction of in-band transmit/receive interference should occur. In some embodiments, there are alternative ways to reduce interference rather than a large guard band, such as transmission power distribution control, which will be discussed below.

Figure 5:
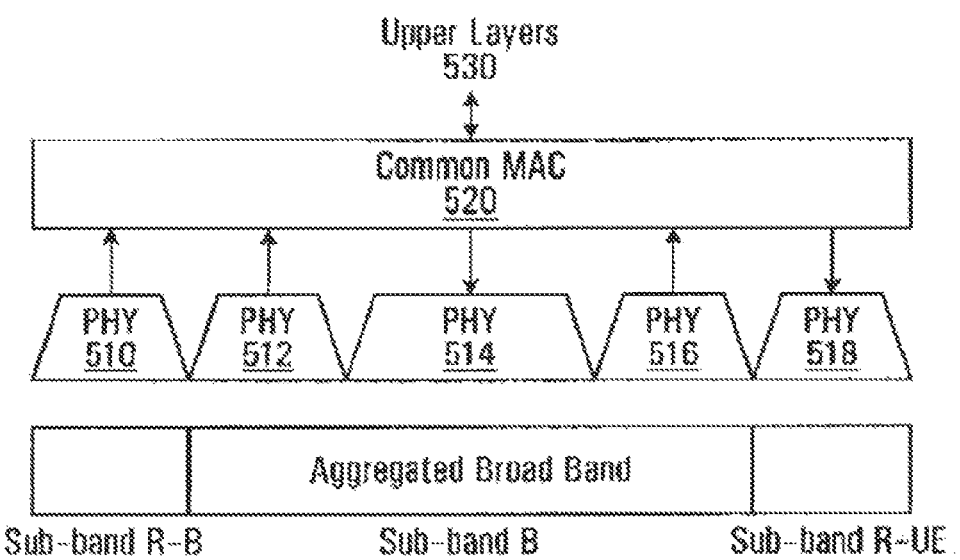
FIG. 5 is a schematic diagram representing different layers utilized in network communications for an example of a contiguous spectrum aggregation according to an embodiment of the invention.

FIG. 5 illustrates a schematic diagram representing different layers utilized in network communications. FIG. 5 is similar in some respects to FIG. 2. The main difference being that FIG. 2 illustrates non-contiguous carriers in the aggregated spectrum, while FIG. 5 illustrates a contiguous group of sub-bands in the aggregated spectrum. In the physical layer (PHY), the respective sub-bands, Sub-band R-UE 510, Sub-band B 512,514,516 and Sub-band R-B 518, are illustrated as separate respective sub-bands, which collectively occupy the entire spectrum. The MAC layer 520 is illustrated as common to all the PHY layer sub-bands. The common MAC layer is illustrated as being in communication with upper layers 530 of the network.

In some embodiments, the size of Sub-band R-B may be adjusted according to the bandwidth requirement for communications between the base station and the at least one relay station.

In some embodiments, the size of Sub-band R-UE may be adjusted according to the bandwidth requirement for communications between a relay station and at least one mobile station with which the relay station is communicating.

In some embodiments, the size of Sub-band B may be adjusted according to the bandwidth requirement for communications between the base station and at least one mobile station one hop away from the base station with which the base station is communicating.

In some embodiments, for supporting legacy mobile stations, in particular, but not limited to the case in which legacy mobile stations are allocated specific carriers that may not align with desired sub-bands in an LTE-A enabled network, the locations of Sub-band R-B and Sub-band R-UE may change from time to time.

In some embodiments, the change of sub-band locations to support legacy users (sub-band hopping) of relay links may occur such that the change may occur on a time slot by time slot basis. In some embodiments, several consecutive time slots have a first sub-band location arrangement and a subsequent one or more consecutive time slots have a second sub-band location arrangement, which is different than the first sub-band location arrangement, to support the legacy mobile stations. This arrangement of time slots may be repeated for the first and second sub-band location arrangements. In some embodiments, the second sub-band location arrangement of subsequent repetitions of the second sub-band location arrangement may change over time. In some embodiments, the number of time slots of either the first or second sub-band location arrangements can vary in number.

In some embodiments, some sub-band locations of the bandwidth use time division duplexing to separate relay station reception and transmission in the time domain to support legacy mobile stations, while other sub-band locations maintain a non-interrupted transmission and reception of communications between the relay station and the base station and/or between the relay station and one or more mobile station. In a particular example, referring to the arrangement of FIG. 5, in a first time slot a relay station receives communication on Sub-band R-B 518 from a base station, but does not transmit on Sub-band R-B 518 to the base station, and in a second time slot the relay station transmits communication on Sub-band R-B 518 to the base station, but does not receive on Sub-band R-B 518 from the base station.

FED In-Band Relay

One manner of maintaining non-interrupted bi-directional links between a base station and a relay station as well as bi-directional links between the relay station and one or more mobile station is a FDD in-band implementation.

Referring to FIGS. 6a and 6b, an FDD in-band implementation for contiguous aggregation spectrum will now be described.

FIG. 6a illustrates a block diagram representation of a base station (eNB) 602 communicating via a relay station (RN) 604 with a mobile station (UE) 606 in a down link direction from the base station 602 to the mobile station 606. For a particular time slot T1, on a DL frequency band F1, the relay station 604 can simultaneously receive data from the base station 602 on Sub-band R-$B_{DL}$ and transmit data to the mobile station 606 on Sub-band R-$UE_{DL}$. Data transmitted from the base station 602 to mobile stations one hop away (not shown) from the base station 602 are transmitted on Sub-band $B_{DL}$ within the in-band spectrum. As these signals do not dissipate at a distance equal to the relay station 604, they are illustrated continuing onto the mobile station 606. This does not necessarily mean that Carrier $B_{DL}$ will reach the mobile station that the relay station is communicating with. Carrier $B_{DL}$ is illustrated to indicate potential interference with Carrier R-$B_{DL}$ and Carrier R-$UE_{DL}$.

In some embodiments, the locations of different sub-bands are maintained in the same positions for each time slot. In some embodiments, the locations of different sub-bands are in different positions, in a similar manner to the different carrier positioning described above for the non-contiguous embodiments. Such embodiments may be useful in supporting legacy mobile stations.

FIG. 6b illustrates a block diagram representation of the base station 602 communicating via the relay station 604 with the mobile station 606 in an uplink direction from the mobile station 606 to the base station 602. For the time slot T1, on a UL frequency band F2, the relay station 604 can simultaneously receive data from the mobile station 606 on Sub-band R-$UE_{UL}$ and transmit data to the base station 602 on Sub-band R-$B_{UL}$. Data transmitted from the mobile stations one hop away (not shown) from the base station 602 to the base station 602 are transmitted on Sub-band $B_{UL}$ within the in-band spectrum. These signals may typically originate close to the base station or close to the relay station, but they are illustrated between the mobile station 606 and the base station 602. Carrier $B_{UL}$ is illustrated to indicate potential interference with Carrier $R\text{-}B_{UL}$ and Carrier $R\text{-}UE_{UL}$.

In some embodiments, the locations of different sub-bands are maintained in the same positions for each time slot. In some embodiments, the locations of sub-bands are in different positions.

FIG. 6c illustrates an example spectrum pertaining to FIGS. 6a and 6b. FIG. 6c illustrates for a given time slot T1 a DL frequency band F1, including Sub-band $R\text{-}UE_{DL}$, Sub-band $B_{DL}$ and Sub-band $R\text{-}B_{DL}$ and an UL frequency band F2, including Sub-band $R\text{-}UE_{UL}$, Sub-band $B_{UL}$ and Sub-band $R\text{-}B_{UL}$.

In some embodiments, any of Sub-band $R\text{-}B_{DL}$, Sub-band $R\text{-}UE_{DL}$, Sub-band $R\text{-}B_{UL}$ and Sub-band $R\text{-}UE_{UL}$ can be re-used by the base station and relay station to further improve the spectrum efficiency. For example, in a base station transmitting over multiple sectors, sub-band $R\text{-}B_{DL}$ (or $R\text{-}B_{UL}$) may be reused in sectors that are well separated such that little to no interference would occur. Similarly, for a given base station, in sectors that are not in close proximity, Sub-band $R\text{-}UE_{DL}$ (or $R\text{-}UE_{UL}$) may be re-used between relay stations and mobile stations.

TDD In-Band Relay

Another manner of maintaining non-interrupted bi-directional links between a base station and a relay station as well as bi-directional links between the relay station and one or more mobile station during DL and UL sub-frames is a TDD in-band implementation.

Referring to FIGS. 7a and 7b, a TDD in-band implementation for contiguous aggregation spectrum will now be described.

FIG. 7a illustrates a block diagram representation of a base station (eNB) 702 communicating via a relay station (RN) 704 with a mobile station (UE) 706 in a down link direction from the base station 702 to the mobile station 706. For a DL time slot T1, on a frequency band F1, the relay station 704 can simultaneously receive data from the base station 702 on Sub-band R-B and transmit data to the mobile station 706 on Sub-band R-UE. Data transmitted from the base station 702 to mobile stations one hop away (not shown) from the base station 702 are transmitted on Sub-band B within the in-band spectrum. These signals may typically originate close to the base station or close to the relay station, but they are illustrated between the mobile station 706 and the base station 702. Carrier B is illustrated to indicate potential interference with Carrier R-B and Carrier R-UE.

In some embodiments, such an implementation occurs with the locations of sub-bands being maintained in the same positions for each time slot. In some embodiments, such an implementation occurs with the locations of sub-bands having different positions.

FIG. 7b illustrates a block diagram representation of the base station 702 communicating via the relay station 704 with the mobile station 706 in an uplink direction from the mobile station 706 to the base station 702. For a UL time slot T2, on the frequency band F1, the relay station 704 can simultaneously receive data from the mobile station 706 on Sub-band R-UE and transmit data to the base station 702 on Sub-band R-B. Data transmitted from the mobile stations one hop away (not shown) from the base station 702 to the base station 702 are transmitted on Sub-band B within the in-band spectrum. These signals may typically originate close to the base station or close to the relay station, but they are illustrated between the mobile station 706 and the base station 702. Carrier B is illustrated to indicate potential interference with Carrier R-B and Carrier R-UE.

In some embodiments, the locations of different sub-bands are maintained in the same positions for each time slot. In some embodiments, the locations of different sub-bands are in different positions, as described above.

FIG. 7c illustrates an example spectrum for each of two time slots as described above with regard to FIGS. 7a and 7b. FIG. 7c illustrates a first time slot T1 in which DL communications occur on frequency band F1, which includes Sub-band R-UE, Sub-band B and Sub-band R-B and a second time slot T2 in which UL communications occur on frequency band 71, which includes Sub-band R-UE, Sub-band B and Sub-band R-B.

While a single base station, single relay station and single mobile station are illustrated in FIGS. 6a, 6b, 7a and 7b, it is to be understood that a network may have multiple base stations, each base station communicating with one or more relay stations and possibly one or more one hop away mobile stations, each relay station communicating with one or more mobile station and possibly one or more second relay stations that may communicate with mobile stations.

In some embodiments, Sub-band R-B and Sub-band R-UE can be re-used by the base station and relay station to further improve the spectrum efficiency.

Figure 8:
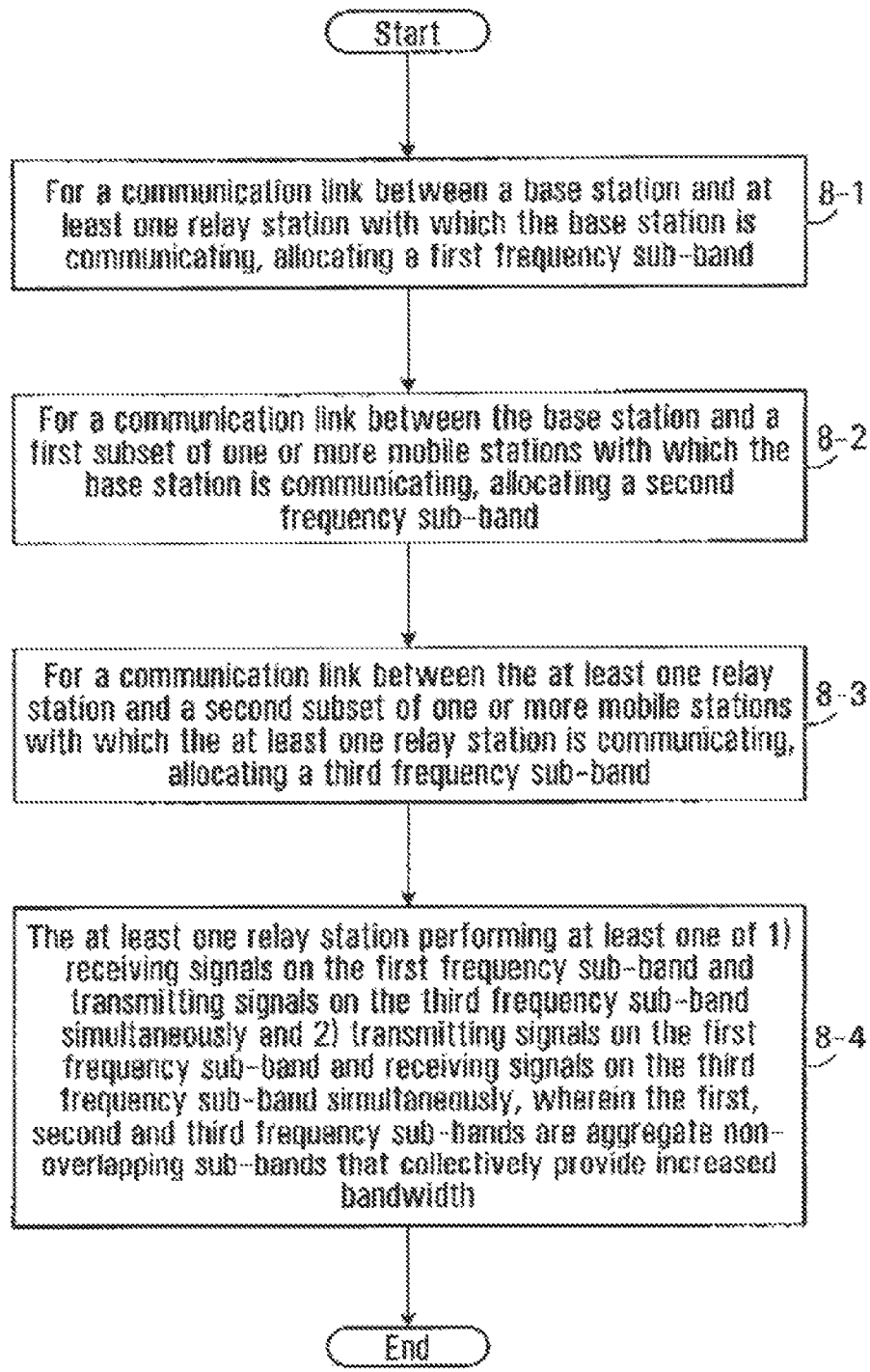
FIG. 8 is a flow chart representing an example of a method according to an embodiment of the invention.

A method for use by a relay station will now be described with regard to FIG. 8. A first step 8-1 of the method involves for a communication link between a base station and at least one relay station with which the base station is communicating, allocating a first frequency sub-band. A second Step 8-2 of the method involves for a communication link between the base station and a first subset of one or more mobile stations with which the base station is communicating, allocating a second frequency sub-band. A third step 8-3 of the method involves for a communication link between the at least one relay station and a second subset of one or more mobile stations with which the at least one relay is communicating, allocating a third frequency sub-band. A fourth step 8-4 of the method involves the at least one relay station performing at least one of: receiving signals on the first frequency sub-band and transmitting signals on the third frequency sub-band simultaneously; and transmitting signals on the first frequency sub-band and receiving signals on the third frequency sub-band simultaneously. The first, second and third frequency sub-bands are aggregate non-overlapping sub-bands that collectively provide increased bandwidth.

In some embodiments, one or more of the first, second and third frequency sub-bands are first, second or third carrier frequencies, respectively. In some embodiments, one or more of the first, second or third carrier frequencies are non-contiguous within the aggregate increased bandwidth.

In some embodiments, the first, second and third frequency sub-bands are contiguous sub-bands within a within the aggregate increased bandwidth.

In some embodiments, at least one of the first and third sub-bands is a dedicated sub-band. In some embodiments, at least one of the first and third sub-bands is dynamically assigned to a different sub-band than the dedicated first or third sub-band, respectively. In some embodiments, the bandwidth of at least one of the first, second and third sub-bands is variable in size and the bandwidth is dynamically assigned.

In a FDD implementation, allocating the first frequency sub-band comprises allocating in a down link (DL) frequency band a first DL frequency sub-band and in an uplink (UL) frequency band a first UL frequency sub-band; allocating the second frequency sub-band comprises allocating in the DL frequency band a second DL frequency sub-band and in the UL frequency band a second UL frequency sub-band; allocating the third frequency sub-band comprises allocating in the DL frequency band a third DL frequency sub-band and in the UL frequency band a third UL frequency sub-band; the at least one relay station performing one or more of receiving signals on the first DL frequency sub-band, transmitting signals on the third DL frequency sub-band, transmitting signals on the first UL frequency sub-band and receiving signals on the third UL frequency sub-band simultaneously in a same time slot.

In a TDD implementation, in a first time slot for down link (DL) communications, allocating in a frequency band the first frequency sub-band, the second frequency sub-band and the third frequency sub-band; in a second time slot for uplink (UL) communications, allocating in the frequency band the first frequency sub-band, the second frequency sub-band and the third frequency sub-band; the at least one relay station performing; receiving signals on the first frequency sub-band and transmitting signals on the third frequency sub-band simultaneously during the first time slot; and transmitting signals on the first frequency sub-band and receiving signals on the third frequency sub-band simultaneously in the second time slot.

A similar method to that described above may be implemented by the base station with which the relay station is communicating. In some embodiments, the base station is responsible for allocating the sub-bands and/or carriers, for use in DL and UL communications between the base station and relay station, between the base station and one hop away mobile stations, between the relay station and additional relay stations two hops away from the base station and between the relay station and mobile stations with which the relay station communicates. Once the base station has allocated the sub-bands and/or carriers, the base station notifies the relay station so that the relay station knows which sub-bands and/or carriers it is transmitting/receiving on. The relay station may further forward this information along to mobile stations with which the relay station communicates. The base station may then be responsible for dynamically assigning different sub-bands and/or carriers as necessary, for example in the case of legacy mobiles, as described above.

Furthermore, a system including at least one base station, at least relay station and at least one mobile station, may collectively perform the method described above.

Tx/Rx Guard Gap Reduction

In some embodiments of the invention, transmission power distribution control is applied to reduce the interference between transmissions and receptions in the relay station.

Figure 9:
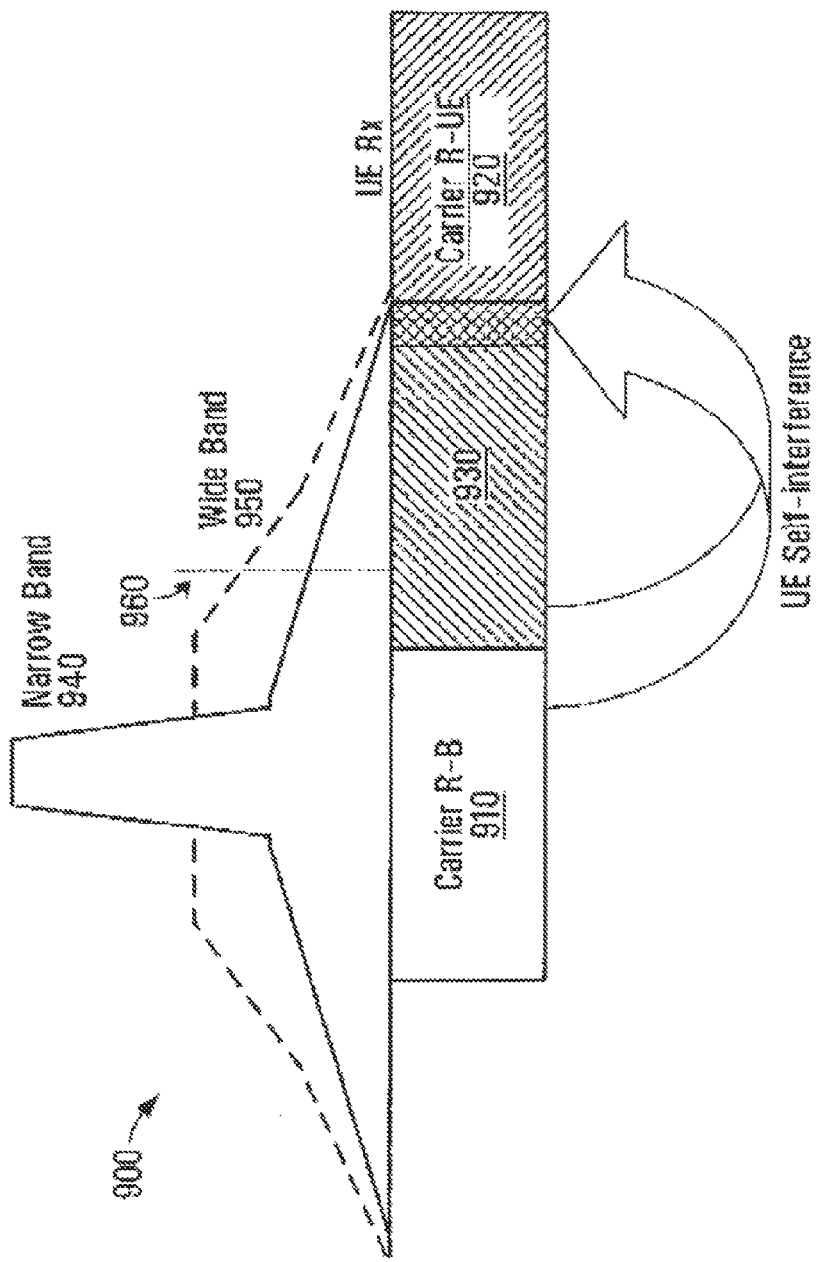
FIG. 9 is an example of an aggregated spectrum illustrating transmission power distribution control according to an aspect of the invention.

FIG. 9 illustrates an example of an aggregated spectrum 900 used in conjunction with a relay station in which Carrier R-E 910 and Carrier R-UE 920 are separated by a guard band 930. Such a guard band may include one or more carriers that are not being used, or one or more carriers that may be used for some type of communication signal. For example, as described above in FIG. 2, at least one carrier between Carrier R-B 910 and carrier R-UE 920 may be used for communications between the base station and one hop away mobile station.

In some embodiments, controlling the transmit power and the bandwidth of communications from the base station may enable the guard band to be reduced. Two formats of signal are illustrated as being transmitted on Carrier R-B, a narrow band, higher peak power signal, indicated at 940, and a wider band, lower peak power signal, indicated at 950. Signal 940 has a higher peak power and narrower bandwidth than signal 950. The narrower bandwidth of signal 940 results in a lower power in an area of guard band 930 than that of signal 950. For example, at a location in the spectrum indicated at 960, the power of the narrow band signal 940 is half the level of the wideband signal 950, with respect to the base level of the two signals. Therefore, since the narrow band signal 940 has a lower power at a same location in the guard band 930, in comparison to the wide band signal 950, the two carrier signals, Carrier R-B 810 and Carrier R-UE 820, could use a smaller guard band, for a similar level of transmit/receive interference reduction control.

In some embodiments, the narrow band signal with higher power may be useful when the desired target node, i.e. the relay station is far away from the base station. In some embodiments, the wide band signal with lower power may be useful when the desired target node, i.e. the relay station is in close proximity to the base station. However, the narrow band signal with higher power may be used when the desired target node, i.e. the relay station is in close proximity to the base station, but a reduced guard band is desired between the carriers used by the relay station for communicating with the base station and mobile stations.

In some embodiments, the relay station may use similar transmission power distribution control for transmissions to the base station, mobile stations, and other relay stations.

Description of Example Components of a Communication System

Figure 10:
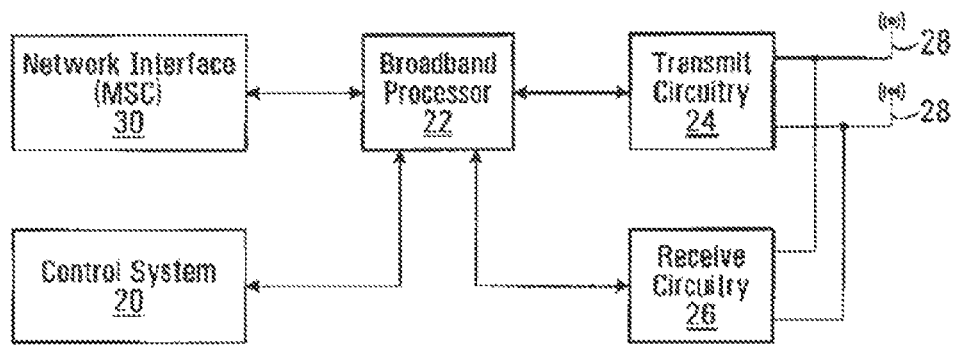
FIG. 10 is a block diagram of an example base station that might be used to implement some embodiments of the present 5 application.

With reference to FIG. 10, an example of a base station 14 is illustrated. The base station 14 generally includes a control system 20, a baseband processor 22, transmit circuitry 24, receive circuitry 26, multiple antennas 28, and a network interface 30. The receive circuitry 26 receives radio frequency signals bearing information from one or more remote transmitters provided by mobile terminals 16 (illustrated in FIG. 11) and relay stations 15 (illustrated in FIG. 12). A low noise amplifier and a filter (not shown) may cooperate to amplify and remove broadband interference from the signal for processing. Downconversion and digitization circuitry (not shown) will then downconvert the filtered, received signal to an intermediate or baseband frequency signal, which is then digitized into one or more digital streams.

The baseband processor 22 processes the digitized received signal to extract the information or data bits conveyed in the received signal. This processing typically comprises demodulation, decoding, and error correction operations. As such, the baseband processor 22 is generally implemented in one or more digital signal processors (DSPs) or application-specific integrated circuits (ASICs). The received information is then sent across a wireless network via the network interface 30 or transmitted to another mobile terminal 16 serviced by the base station 14, either directly or with the assistance of a relay 15.

On the transmit side, the baseband processor 22 receives digitized data, which may represent voice, data, or control information, from the network interface 30 under the control of control system 20, and encodes the data for transmission. The encoded data is output to the transmit circuitry 24, where it is modulated by one or more carrier signals having a desired transmit frequency or frequencies. A power amplifier (not shown) will amplify the modulated carrier signals to a level appropriate for transmission, and deliver the modulated carrier signals to the antennas 28 through a matching network (not shown). Modulation and processing details are described in greater detail below.

Figure 11:
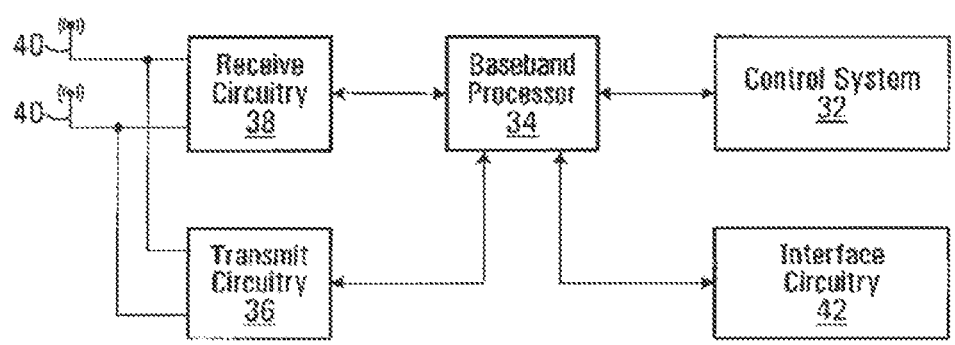
FIG. 11 is a block diagram of an example wireless terminal that might be used to implement some embodiments of the present application.

With reference to FIG. 11, an example of a mobile terminal 16 is illustrated. Similarly to the base station 14, the mobile terminal 16 will include a control system 32, a baseband processor 34, transmit circuitry 36, receive circuitry 38, multiple antennas 40, and user interface circuitry 42. The receive circuitry 38 receives radio frequency signals bearing information from one or more base stations 14 and relays 15. A low noise amplifier and a filter (not shown) may cooperate to amplify and remove broadband interference from the signal for processing. Downconversion and digitization circuitry (not shown) will then downconvert the filtered, received signal to an intermediate or baseband frequency signal, which is then digitized into one or more digital streams.

The baseband processor 34 processes the digitized received signal to extract the information or data bits conveyed in the received signal. This processing typically comprises demodulation, decoding, and error correction operations. The baseband processor 34 is generally implemented in one or more digital signal processors (DSPs) and application specific integrated circuits (ASICs).

For transmission, the baseband processor 34 receives digitized data, which may represent voice, video, data, or control information, from the control system 32, which it encodes for transmission. The encoded data is output to the transmit circuitry 36, where it is used by a modulator to modulate one or more carrier signals that is at a desired transmit frequency or frequencies. A power amplifier (not shown) will amplify the modulated carrier signals to a level appropriate for transmission, and deliver the modulated carrier signal to the antennas 40 through a matching network (not shown), Various modulation and processing techniques available to those skilled in the art are used for signal transmission between the mobile terminal and the base station, either directly or via the relay station.

In OFDM modulation, the transmission band is divided into multiple, orthogonal carrier waves. Each carrier wave is modulated according to the digital data to be transmitted. Because OFDM divides the transmission band into multiple carriers, the bandwidth per carrier decreases and the modulation time per carrier increases. Since the multiple carriers are transmitted in parallel, the transmission rate for the digital data, or symbols, on any given carrier is lower than when a single carrier is used.

OFDM modulation utilizes the performance of an Inverse Fast Fourier Transform (IFFT) on the information to be transmitted. For demodulation, the performance of a Fast Fourier Transform (FFT) on the received signal recovers the transmitted information. In practice, the IFFT and FFT are provided by digital signal processing carrying out an Inverse Discrete Fourier Transform (IDFT) and Discrete Fourier Transform (DFT), respectively. Accordingly, the characterizing feature of OFDM modulation is that orthogonal carrier waves are generated for multiple bands within a transmission channel. The modulated signals are digital signals having a relatively low transmission rate and capable of staying within their respective bands. The individual carrier waves are not modulated directly by the digital signals. Instead, all carrier waves are modulated at once by IFFT processing.

In operation, OFDM is preferably used for at least downlink transmission from the base stations 14 to the mobile terminals 16. Each base station 14 is equipped with "n" transmit antennas 28 (n>=1), and each mobile terminal 16 is equipped with "m" receive antennas 40 (m>=1). Notably, the respective antennas can be used for reception and transmission using appropriate duplexers or switches and are so labeled only for clarity.

When relay stations 15 are used, OFDM is preferably used for downlink transmission from the base stations 14 to the relays 15 and from relay stations 15 to the mobile terminals 16.

Figure 12:
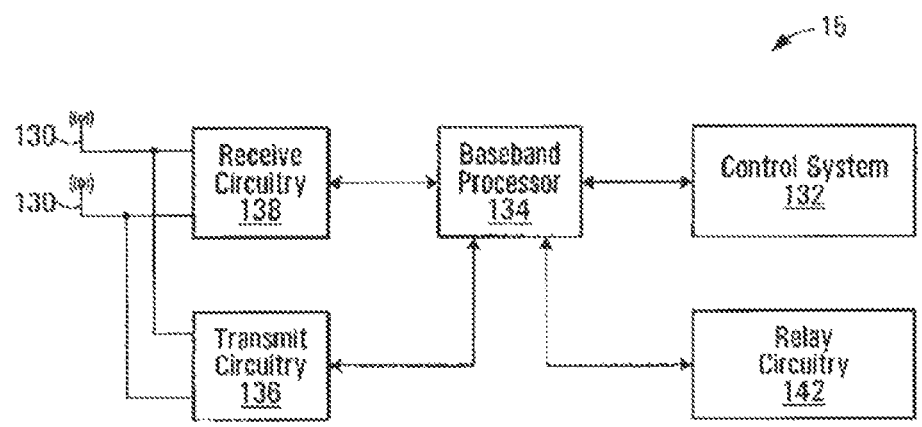
FIG. 12 is a block diagram of an example relay station that might be used to implement some embodiments of the present application.

With reference to FIG. 12, an example of a relay station 15 is illustrated. Similarly to the base station 14, and the mobile terminal 16, the relay station 15 will include a control system 132, a baseband processor 134, transmit circuitry 136, receive circuitry 138, multiple antennas 130, and relay circuitry 142. The relay circuitry 142 enables the relay 14 to assist in communications between a base station 16 and mobile terminals 16. The receive circuitry 138 receives radio frequency signals bearing information from one or more base stations 14 and mobile terminals 16. A low noise amplifier and a filter (not shown) may cooperate to amplify and remove broadband interference from the signal for processing. Downconversion and digitization circuitry (not shown) will then downconvert the filtered, received signal to an intermediate or baseband frequency signal, which is then digitized into one or more digital streams.

The baseband processor 134 processes the digitized received signal to extract the information or data bits conveyed in the received signal. This processing typically comprises demodulation, decoding, and error correction operations. The baseband processor 134 is generally implemented in one or more digital signal processors (DSPs) and application specific integrated circuits (ASICs).

For transmission, the baseband processor 134 receives digitized data, which may represent voice, video, data, or control information, from the control system 132, which it encodes for transmission. The encoded data is output to the transmit circuitry 136, where it is used by a modulator to modulate one or more carrier signals that is at a desired transmit frequency or frequencies. A power amplifier (not shown) will amplify the modulated carrier signals to a level appropriate for transmission, and deliver the modulated carrier signal to the antennas 130 through a matching network (not shown). Various modulation and processing techniques available to those skilled in the art are used for signal transmission between the mobile terminal and the base station, either directly or indirectly via a relay station, as described above.

Figure 13:
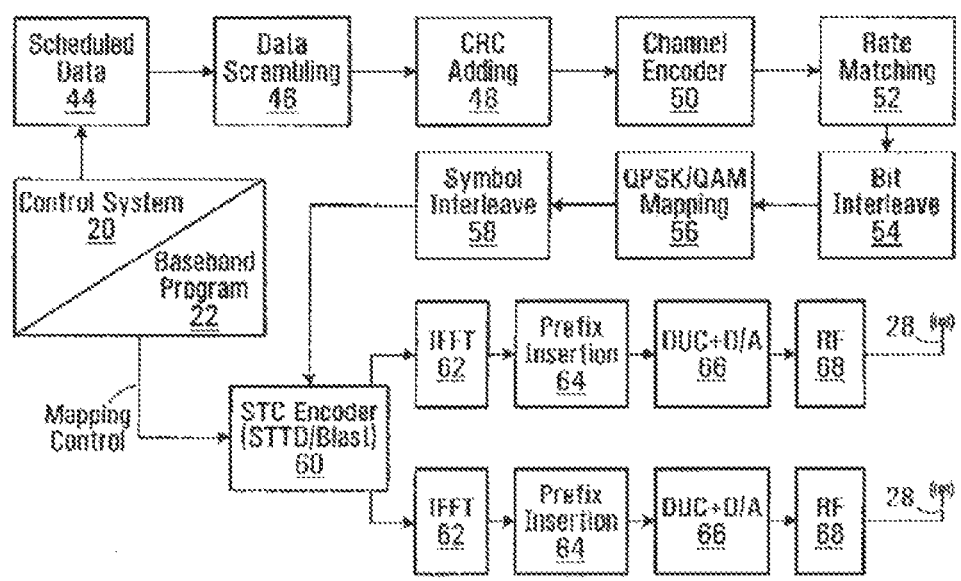
FIG. 13 is a block diagram of a logical breakdown of an example OFDM transmitter architecture that might be used to implement some embodiments of the present application.

With reference to FIG. 13, a logical OFDM transmission architecture will be described. Initially, the base station controller 10 will send data to be transmitted to various mobile terminals 16 to the base station 14, either directly or with the assistance of a relay station 15. The base station 14 may use the channel quality indicators (CQIs) associated with the mobile terminals to schedule the data for transmission as well as select appropriate coding and modulation for transmitting the scheduled data. The CQIs may be directly from the mobile terminals 16 or determined at the base station 14 based on information provided by the mobile terminals 16. In either case, the CQI for each mobile terminal 16 is a function of the degree to which the channel amplitude (or response) varies across the OFDM frequency band.

Scheduled data 44, which is a stream of bits, is scrambled in a manner reducing the peak-to-average power ratio associated with the data using data scrambling logic 46. A cyclic redundancy check (CRC) for the scrambled data is determined and appended to the scrambled data using CRC adding logic 48. Next, channel coding is performed using channel encoder logic 50 to effectively add redundancy to the data to facilitate recovery and error correction at the mobile terminal 16. Again, the channel coding for a particular mobile terminal 16 is based on the CQI. In some implementations, the channel encoder logic 50 uses known Turbo encoding techniques. The encoded data is then processed by rate matching logic 52 to compensate for the data expansion associated with encoding.

Bit interleaver logic 54 systematically reorders the bits in the encoded data to minimize the loss of consecutive data bits. The resultant data bits are systematically mapped into corresponding symbols depending on the chosen baseband modulation by mapping logic 56. Preferably, Quadrature Amplitude Modulation (QAM) or Quadrature Phase Shift Key (QPSK) modulation is used. The degree of modulation is preferably chosen based on the CQI for the particular mobile terminal. The symbols may be systematically reordered to further bolster the immunity of the transmitted signal to periodic data loss caused by frequency selective fading using symbol interleaves logic 58.

At this point, groups of bits have been mapped into symbols representing locations in an amplitude and phase constellation. When spatial diversity is desired, blocks of symbols are then processed by space-time block code (STC) encoder logic 60, which modifies the symbols in a fashion making the transmitted signals more resistant to interference and more readily decoded at a mobile terminal 16. The STC encoder logic 60 will process the incoming symbols and provide "n" outputs corresponding to the number of transmit antennas 28 for the base station 14. The control system 20 and/or baseband processor 22 as described above with respect to FIG. 13 will provide a mapping control signal to control STC encoding. At this point, assume the symbols for the "n" outputs are representative of the data to be transmitted and capable of being recovered by the mobile terminal 16.

For the present example, assume the base station 14 has two antennas 28 (n=2) and the STC encoder logic 60 provides two output streams of symbols. Accordingly, each of the symbol streams output by the STC encoder logic 60 is sent to a corresponding IFFT processor 62, illustrated separately for ease of understanding. Those skilled in the art will recognize that one or more processors may be used to provide such digital signal processing, alone or in combination with other processing described herein. The IFFT processors 62 will preferably operate on the respective symbols to provide an inverse Fourier Transform. The output of the IFFT processors 62 provides symbols in the time domain. The time domain symbols are grouped into frames, which are associated with a prefix by prefix insertion logic 64. Each of the resultant signals is up-converted in the digital domain to an intermediate frequency and converted to an analog signal via the corresponding digital up-conversion (DUC) and digital-to-analog (D/A) conversion circuitry 66. The resultant (analog) signals are then simultaneously modulated at the desired RF frequency, amplified, and transmitted via the RF circuitry 68 and antennas 28. Notably, pilot signals known by the intended mobile terminal 16 are scattered among the sub-carriers. The mobile terminal 16, which is discussed in detail below, will use the pilot signals for channel estimation.

Figure 14:
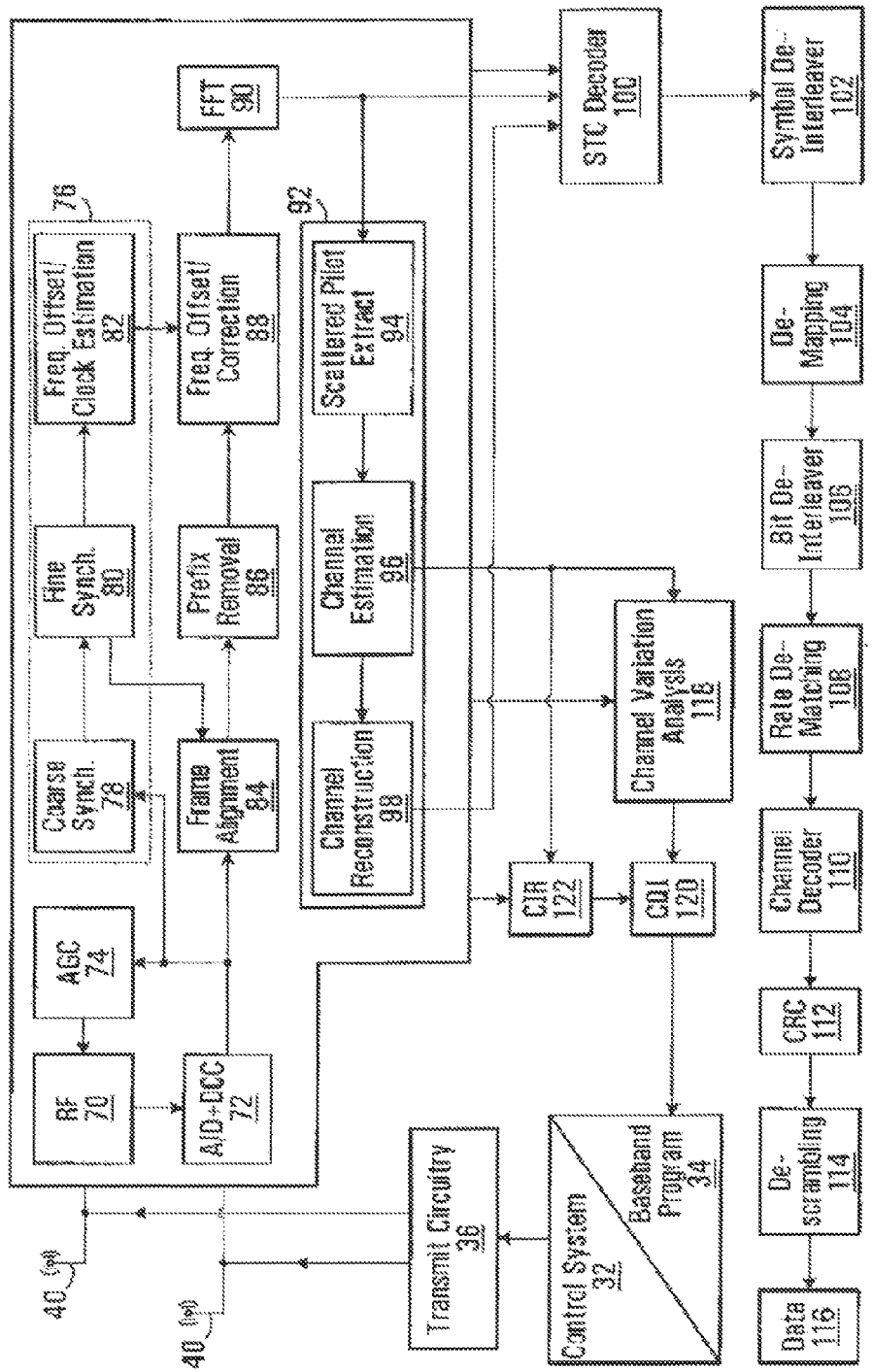
FIG. 14 is a block diagram of a logical breakdown of an example OFDM receiver architecture that might be used to implement some embodiments of the present application.
Figure 15A:
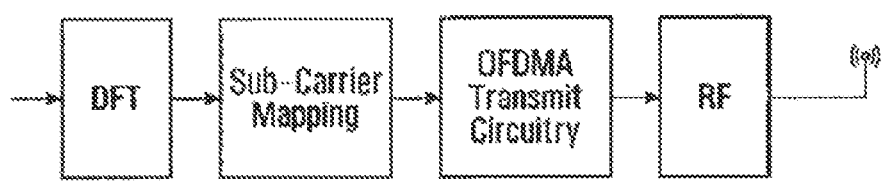
FIG. 15a is a block diagram of an SC-FDMA transmitter used to implement some embodiments of the present application.
Figure 15B:
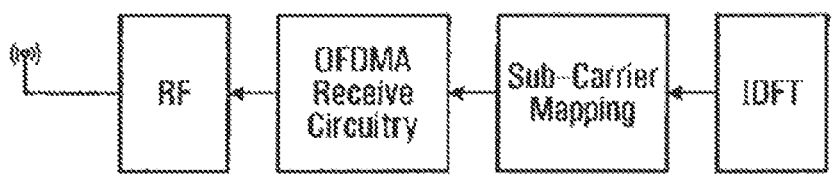
FIG. 15b is a block diagram of an SC-FDMA receiver used to implement some embodiments of the present application.

Reference is now made to FIG. 14 to illustrate reception of the transmitted signals by a mobile terminal 16, either directly from base station 14 or with the assistance of relay 15. Upon arrival of the transmitted signals at each of the antennas 40 of the mobile terminal 16, the respective signals are demodulated and amplified by corresponding RF circuitry 70. For the sake of conciseness and clarity, only one of the two receive paths is described and illustrated in detail. Analog-to-digital (A/D) converter and down-conversion circuitry 72 digitizes and downconverts the analog signal for digital processing. The resultant digitized signal may be used by automatic gain control circuitry (AGC) 74 to control the gain of the amplifiers in the RF circuitry 70 based on the received signal level.

Initially, the digitized signal is provided to synchronization logic 76, which includes coarse synchronization logic 78, which buffers several OFDM symbols and calculates an auto-correlation between the two successive OFDM symbols. A resultant time index corresponding to the maximum of the correlation result determines a fine synchronization search window, which is used by fine synchronization logic 80 to determine a precise framing starting position based on the headers. The output of the fine synchronization logic 80 facilitates frame acquisition by frame alignment logic 84. Proper framing alignment is important so that subsequent FFT processing provides an accurate conversion from the time domain to the frequency domain. The fine synchronization algorithm is based on the correlation between the received pilot signals carried by the headers and a local copy of the known pilot data. Once frame alignment acquisition occurs, the prefix of the OFDM symbol is removed with prefix removal logic 86 and resultant samples are sent to frequency offset correction logic 88, which compensates for the system frequency offset caused by the unmatched local oscillators in the transmitter and the receiver. Preferably, the synchronization logic 76 includes frequency offset and clock estimation logic 82, which is based on the headers to help estimate such effects on the transmitted signal and provide those estimations to the correction logic 88 to properly process OFDM symbols.

At this point, the OFDM symbols in the time domain are ready for conversion to the frequency domain using FFT processing logic 90. The results are frequency domain symbols, which are sent to processing logic 92. The processing logic 92 extracts the scattered pilot signal using scattered pilot extraction logic 94, determines a channel estimate based on the extracted pilot signal using channel estimation logic 96, and provides channel responses for all sub-carriers using channel reconstruction logic 98. In order to determine a channel response for each of the sub-carriers, the pilot signal is essentially multiple pilot symbols that are scattered among the data symbols throughout the OFDM sub-carriers in a known pattern in both time and frequency. Continuing with FIG. 14, the processing logic compares the received pilot symbols with the pilot symbols that are expected in certain sub-carriers at certain times to determine a channel response for the sub-carriers in which pilot symbols were transmitted. The results are interpolated to estimate a channel response for most, if not all, of the remaining sub-carriers for which pilot symbols were not provided. The actual and interpolated channel responses are used to estimate an overall channel response, which includes the channel responses for most, if not all, of the sub-carriers in the OFDM channel.

The frequency domain symbols and channel reconstruction information, which are derived from the channel responses for each receive path are provided to an STC decoder 100, which provides STC decoding on both received paths to recover the transmitted symbols. The channel reconstruction information provides equalization information to the STC decoder 100 sufficient to remove the effects of the transmission channel when processing the respective frequency domain symbols.

The recovered symbols are placed back in order using symbol de-interleaver logic 102, which corresponds to the symbol interleaver logic 58 of the transmitter. The de-interleaved symbols are then demodulated or de-mapped to a corresponding bitstream using de-mapping logic 104. The bits are then de-interleaved using bit de-interleaver logic 106, which corresponds to the bit interleaver logic 54 of the transmitter architecture. The de-interleaved bits are then processed by rate de-matching logic 108 and presented to channel decoder logic 110 to recover the initially scrambled data and the CRC checksum. Accordingly, CRC logic 112 removes the CRC checksum, checks the scrambled data in traditional fashion, and provides it to the de-scrambling logic 114 for de-scrambling using the known base station de-scrambling code to recover the originally transmitted data 116.

In parallel to recovering the data 116, a CQI, or at least information sufficient to create a CQI at the base station 14, is determined and transmitted to the base station 14. As noted above, the CQI may be a function of the carrier-to-interference ratio (CR), as well as the degree to which the channel response varies across the various sub-carriers in the OFDM frequency band. For this embodiment, the channel gain for each sub-carrier in the OFDM frequency band being used to transmit information is compared relative to one another to determine the degree to which the channel gain varies across the OFDM frequency band. Although numerous techniques are available to measure the degree of variation, one technique is to calculate the standard deviation of the channel gain for each sub-carrier throughout the OFDM frequency band being used to transmit data.

Referring to FIGS. 7(a) and 7(b), examples of an SC-FDMA transmitter and receiver for single-in single-out (SISO) configuration are respectively illustrated in accordance with one embodiment of the present application. In SISO, mobile stations transmit on one antenna and base stations and/or relay stations receive on one antenna. FIGS. 7(a) and 7(b) illustrate the basic signal processing steps needed at the transmitter and receiver for an LTE SC-FDMA uplink. In some embodiments, SC-FDMA (Single-Carrier Frequency Division Multiple Access) is used. SC-FDMA is a modulation and multiple access scheme introduced for the uplink of 3GPP Long Term Evolution (LTE) broadband wireless fourth generation (4G) air interface standards, and the like. SC-FDMA can be viewed as a DFT pre-coded OFDMA scheme, or, it can be viewed as a single carrier (SC) multiple access scheme. There are several similarities in the overall transceiver processing of SC-FDMA and OFDMA. Those common aspects between OFDMA and SC-FDMA are illustrated in the OFDMA TRANSMIT CIRCUITRY and OFDMA RECEIVE CIRCUITRY, as they would be obvious to a person having ordinary skill in the art in view of the present specification. SC-FDMA is distinctly different from OFDMA because of the DFT pre-coding of the modulated symbols, and the corresponding IDFT of the demodulated symbols. Because of this pre-coding, the SC-FDMA sub-carriers are not independently modulated as in the case of the OFDMA sub-carriers. As a result, PAPR of SCFDMA signal is lower than the PAPR of OFDMA signal. Lower PAPR greatly benefits the mobile terminal in terms of transmit power efficiency.

FIGS. 1 and 10 to 15(a) and 15(b) provide one specific example of a communication system that could be used to implement embodiments of the application. It is to be understood that embodiments of the application can be implemented with communications systems having architectures that are different than the specific example, but that operate in a manner consistent with the implementation of the embodiments as described herein.

Numerous modifications and variations of the present invention are possible in light of the above teachings. It is therefore to be understood that within the scope of the appended claims, the invention may be practiced otherwise than as specifically described herein.

What is claimed is:

1. A relay station, comprising:
at least one antenna,
transmit circuitry coupled to the at least one antenna and configured to:
  transmit signals on one or more first frequency carriers to a base station; and
  transmit signals on one or more second frequency carriers to a first subset of one or more mobile stations; and
receive circuitry coupled to the at least one antenna and configured to:
  receive signals on the one or more first frequency carriers from the base station; and
  receive signals on the one or more second frequency carriers from the first subset of the one or more mobile stations;
wherein one or more third frequency carriers are allocated for a communication link between the base station and a second subset of the one or more mobile stations;
wherein the first, second, and third frequency carriers are separate, non-overlapping carriers that collectively provide increased bandwidth;
wherein the first, second and third carriers are long term evolution (LTE) carriers each comprising one or more of orthogonal frequency modulation (OFDM) and Single-Carrier Frequency Division Multiple Access (SC-FDMA) and are separated by at least a guard band; and
wherein a number of carriers included in at least one of the first, second, and third carriers is changed.

2. The relay station of claim 1,
wherein at least one of the first frequency carriers comprises a first down link (DL) frequency carrier and a first up link (UL) frequency carrier;
wherein at least one of the second frequency carriers comprises a second down link (DL) frequency carrier and a second up link (UL) frequency carrier; and
wherein at least one of the third frequency carriers comprises a third down link (DL) frequency carrier and a third up link (UL) frequency carrier.

3. The relay station of claim 2,
wherein the transmit circuitry is further configured to:
  transmit the signals to the base station on the first UL frequency carrier; and
  transmit the signals to the first subset of the one or more mobile stations on the second DL frequency carrier; and
wherein the receive circuitry is further configured to:
  receive the signals from the base station on the first DL frequency carrier; and
  receive the signals form the first subset of the one or more mobile stations of the second UL frequency carrier.

4. The relay station of claim 1, wherein the relay station is further configured to:
in a first time slot:
  receive the signals from the base station on the one or more first frequency carriers; and transmit the signals to the first subset of the one or more mobile stations on the one or more second frequency carriers;
wherein the second set of one or more mobile stations are configured to receive signals from the base station on the one or more third frequency carriers; and
in a second time slot:
transmit the signals to the base station on the one or more first frequency carriers; and
receive the signals from the first subset of the one or more mobile stations on the one or more second frequency carriers;
wherein the second set of one or more mobile stations are configured to transmit signals to the base station on the one or more third frequency carriers.

5. The relay station of claim 4,
wherein, during the first time slot, the relay station is configured to receive the signals from the base station and transmit the signals to the first subset of the one or more mobile stations simultaneously; and
wherein, during the second time slot, the relay station is configured to transmit the signals to the base station and receive signals form the first subset of the one or more mobile stations simultaneously.

6. The relay station of claim 1, wherein the relay station is further configured to:
apply transmission power distribution control to reduce the interference between transmissions and receptions of the relay station.

7. The relay station of claim 6,
wherein to apply transmission power distribution control, the relay station is further configured to transmit the signals on the first or second frequency carriers using a narrow band signal with a higher power than a wide band signal having a lower power.

8. The relay station of claim 1,
wherein one or more of the first, second, and third carrier frequencies are non-contiguous carrier frequencies within the aggregate increased bandwidth.

9. A method, comprising:
a relay station,
transmitting signals on one or more first frequency carriers to a base station;
transmitting signals on one or more second frequency carriers to a first subset of one or more mobile stations;
receiving signals on the one or more first frequency carriers from the base station; and
receiving signals on the one or more second frequency carriers from the first subset of the one or more mobile stations;
wherein one or more third frequency carriers are allocated for a communication link between the base station and a second subset of the one or more mobile stations;
wherein the first, second, and third frequency carriers are separate, non-overlapping carriers that collectively provide increased bandwidth;
wherein the first, second and third carriers are long term evolution (LTE) carriers each comprising one or more of orthogonal frequency modulation (OFDM) and Single-Carrier Frequency Division Multiple Access (SC-FDMA) and are separated by at least a guard band; and
wherein a number of carriers included in at least one of the first, second, and third carriers is changed.

10. The method of claim 9,
wherein at least one of the first frequency carriers comprises a first down link (DL) frequency carrier and a first up link (UL) frequency carrier;
wherein at least one of the second frequency carriers comprises a second down link (DL) frequency carrier and a second up link (UL) frequency carrier; and
wherein at least one of the third frequency carriers comprises a third down link (DL) frequency carrier and a third up link (UL) frequency carrier.

11. The method of claim 10, further comprising:
the relay station,
transmitting the signals to the base station on the first UL frequency carrier;
transmitting signals to the first subset of the one or more mobile stations on the second DL frequency carrier;
receiving the signals from the base station on the first DL frequency carrier; and
receiving the signals form the first subset of the one or more mobile stations of the second UL frequency carrier.

12. The method of claim 9, further comprising:
the relay station, in a first time slot:
receiving the signals from the base station on the one or more first frequency carriers; and
transmitting the signals to the first subset of the one or more mobile stations on the one or more second frequency carriers;
wherein the second set of one or more mobile stations are configured to receive the signals from the base station on the one or more third frequency carriers; and
the relay station, in a second time slot:
transmitting the signals to the base station on the one or more first frequency carriers; and
receiving the signals from the first subset of the one or more mobile stations on the one or more second frequency carriers;
wherein the second set of one or more mobile stations are configured to transmit the signals to the base station on the one or more third frequency carriers.

13. The method of claim 9, further comprising:
the relay station,
applying transmission power distribution control to reduce the interference between transmissions and receptions of the relay station.

14. The method of claim 13,
wherein applying transmission power distribution control comprises:
the relay station,
transmitting signals on the first or second frequency carriers using a narrow band signal with a higher power than a wide band signal having a lower power.

15. The method of claim 9,
wherein one or more of the first, second, and third carrier frequencies are non-contiguous carrier frequencies within the aggregate increased bandwidth.

16. A non-transitory computer readable memory medium storing program instructions executable by a processor of a relay station to:
transmit signals on one or more first frequency carriers to a base station;
transmit signals on one or more second frequency carriers to a first subset of one or more mobile stations;

receive signals on the one or more first frequency carriers from the base station; and receive signals on the one or more second frequency carriers from the first subset of the one or more mobile stations;

wherein one or more third frequency carriers are allocated for a communication link between the base station and a second subset of the one or more mobile stations;

wherein the first, second, and third frequency carriers are separate, non-overlapping carriers that collectively provide increased bandwidth;

wherein the first, second and third carriers are long term evolution (LTE) carriers each comprising one or more of orthogonal frequency modulation (OFDM) and Single-Carrier Frequency Division Multiple Access (SC-FDMA) and are separated by at least a guard band; and wherein a number of carriers included in at least one of the first, second, and third carriers is changed.

17. The non-transitory computer readable memory medium of claim 16, wherein at least one of the first frequency carriers comprises a first down link (DL) frequency carrier and a first up link (UL) frequency carrier;

wherein at least one of the second frequency carriers comprises a second down link (DL) frequency carrier and a second up link (UL) frequency carrier; and wherein at least one of the third frequency carriers comprises a third down link (DL) frequency carrier and a third up link (UL) frequency carrier.

18. The non-transitory computer readable memory medium of claim 17, wherein the program instructions are further executable to:

transmit the signals to the base station on the first UL frequency carrier;

transmit the signals to the first subset of the one or more mobile stations on the second DL frequency carrier;

receive the signals from the base station on the first DL frequency carrier; and receive the signals form the first subset of the one or more mobile stations of the second UL frequency carrier.

19. The non-transitory computer readable memory medium of claim 16, wherein the program instructions are further executable to, in a first time slot:

receive the signals from the base station on the one or more first frequency carriers; and transmit the signals to the first subset of the one or more mobile stations on the one or more second frequency carriers;

wherein the second set of one or more mobile stations are configured to receive the signals from the base station on the one or more third frequency carriers; and wherein the program instructions are further executable to, in a second time slot:

transmit the signals to the base station on the one or more first frequency carriers; and receive the signals from the first subset of the one or more mobile stations on the one or more second frequency carriers;

wherein the second set of one or more mobile stations are configured to transmit the signals to the base station on the one or more third frequency carriers.

20. The non-transitory computer readable memory medium of claim 16, wherein the program instructions are further executable to, wherein the relay station is further configured to:

apply transmission power distribution control to reduce the interference between transmissions and receptions of the relay station.

* * * * *